(12) United States Patent
Konno

(10) Patent No.: US 10,383,585 B2
(45) Date of Patent: Aug. 20, 2019

(54) X-RAY IMAGING APPARATUS

(71) Applicant: HITACHI, LTD., Tokyo (JP)

(72) Inventor: Yasutaka Konno, Tokyo (JP)

(73) Assignee: HITACHI, LTD., Tokyo (JP)

( * ) Notice: Subject to any disclaimer, the term of this patent is extended or adjusted under 35 U.S.C. 154(b) by 396 days.

(21) Appl. No.: 15/502,991

(22) PCT Filed: Aug. 25, 2015

(86) PCT No.: PCT/JP2015/073793
§ 371 (c)(1),
(2) Date: Feb. 9, 2017

(87) PCT Pub. No.: WO2016/042981
PCT Pub. Date: Mar. 24, 2016

(65) Prior Publication Data
US 2017/0231584 A1 Aug. 17, 2017

(30) Foreign Application Priority Data

Sep. 17, 2014 (JP) .................................. 2014-189369

(51) Int. Cl.
*A61B 6/00* (2006.01)
*A61B 6/03* (2006.01)
(Continued)

(52) U.S. Cl.
CPC ............ *A61B 6/4241* (2013.01); *A61B 6/032* (2013.01); *A61B 6/585* (2013.01); *G01N 23/046* (2013.01); *G01T 1/171* (2013.01); *A61B 6/5205* (2013.01)

(58) Field of Classification Search
None
See application file for complete search history.

(56) References Cited

U.S. PATENT DOCUMENTS 9,971,047 B2 * 5/2018 Tamura ................. G01T 1/2985
2010/0270472 A1 * 10/2010 Proksa .................... G01T 1/171
250/371

(Continued)

FOREIGN PATENT DOCUMENTS

CN 103202706 A 7/2013
JP 63-289476 11/1988
(Continued)

OTHER PUBLICATIONS

Chinese official action dated Jun. 12, 2018 in corresponding Chinese Patent Application No. 201580045287.2.
(Continued)

*Primary Examiner* — Hoon K Song
(74) *Attorney, Agent, or Firm* — Cooper & Dunham LLP

(57) ABSTRACT

In an X-ray scanning apparatus including a photon counting type X-ray detection element, in order to perform counted number correction specialized for pile-up with high accuracy, the X-ray scanning apparatus includes an X-ray detector in which a plurality of photon counting type X-ray detection elements are disposed, each of the X-ray detection elements detecting an incident X-ray photon, classifying energy of the X-ray photon into two or more energy ranges, and counting the X-ray photon, and a correction unit that corrects the counted number in the X-ray detection element, in which the correction unit includes a counting error amount determination part that determines a counting error amount in a counted number due to pile-up according to a pile-up occurrence probability in two or more X-ray photons.

19 Claims, 20 Drawing Sheets

|  | ACCURATE COUNT | | | | WRONG COUNT | | CHANGE | |
|---|---|---|---|---|---|---|---|---|
|  | LOW | LOW | HIGH | HIGH | LOW | HIGH | LOW | HIGH |
| CASE 1 | 1 | 1 |  |  | 1 |  | -1 | 0 |
| CASE 2 | 1 | 1 |  |  |  | 1 | -2 | 1 |
| CASE 3 | 1 |  | 1 |  |  | 1 | -1 | 0 |
| CASE 4 |  |  | 1 | 1 |  | 1 | 0 | -1 |

(51) Int. Cl.
    *G01T 1/17*    (2006.01)
    *G01N 23/046*    (2018.01)

(56) References Cited

U.S. PATENT DOCUMENTS

| | | | |
|---|---|---|---|
| 2011/0155899 A1 | 6/2011 | Dror et al. | |
| 2013/0182818 A1 | 7/2013 | Miyazaki | |
| 2015/0287221 A1* | 10/2015 | Takayama | G01N 23/046 |
| | | | 382/131 |
| 2016/0370475 A1* | 12/2016 | Kawata | G01T 1/17 |

FOREIGN PATENT DOCUMENTS

| | | |
|---|---|---|
| JP | 63-298087 | 12/1988 |
| JP | 2011-185716 | 9/2011 |
| JP | 2012-13563 | 1/2012 |
| JP | 2013-516610 | 5/2013 |

OTHER PUBLICATIONS

International Search Report in connection with PCT/JP2015/073793.

* cited by examiner

FIG.8

|  | ACCURATE COUNT | | | | WRONG COUNT | | CHANGE | |
|---|---|---|---|---|---|---|---|---|
|  | LOW | LOW | HIGH | HIGH | LOW | HIGH | LOW | HIGH |
| CASE 1 | 1 | 1 | | | 1 | | -1 | 0 |
| CASE 2 | 1 | 1 | | | | 1 | -2 | 1 |
| CASE 3 | 1 | | 1 | | | 1 | -1 | 0 |
| CASE 4 | | | 1 | 1 | | 1 | 0 | -1 |

FIG.9

| | ACCURATE COUNT | | | WRONG COUNT | | CHANGE | | ACCURATE COUNT | |
|---|---|---|---|---|---|---|---|---|---|
| | LOW | LOW | LOW | HIGH | HIGH | HIGH | LOW | HIGH | LOW | HIGH |
| CASE 1 | 1 | 1 | 1 | | | | 1 | | -2 | 0 |
| CASE 2 | 1 | 1 | 1 | | | | | 1 | -3 | 1 |
| CASE 3-1 | | 1 | 1 | 1 | | | | 1 | -2 | 0 |
| CASE 3-2 | | | 1 | 1 | 1 | | | 1 | -1 | -1 |
| CASE 4 | | | | 1 | 1 | 1 | | 1 | 0 | -2 |

| CASE | INCIDENT X-RAY 1 | INCIDENT X-RAY 2 | CLASSIFICATION RESULT | CHANGE RESULT |
|---|---|---|---|---|
| 1 | k-TH($1 \leq k \leq N$) | k-TH($1 \leq k \leq N$) | k-TH | k-TH-1 |
| 2 | k-TH($1 \leq k \leq N-1$) | k-TH($1 \leq k \leq N-1$) | n-TH($k+1 \leq n \leq N$) | k-TH-2 n-TH+1 |
| 3 | k-TH($1 \leq k \leq N-1$) | n-TH($k+1 \leq n \leq N$) | n-TH | k-TH-1 |
| 4 | k-TH($1 \leq k \leq N-1$) | n-TH($k+1 \leq n \leq N$) | m-TH($k+1 \leq m \leq N$) | k-TH-1 n-TH+1 m-TH+1 |

(b)

| CASE | INCIDENT X-RAY 1 (n-TH) | INCIDENT X-RAY 2 (MAXIMUM ENERGY RANGE IS k-TH (k≥n) OTHER THAN n-TH) | CLASSIFICATION RESULT | CHANGE RESULT |
|---|---|---|---|---|
| 1 | Q($2 \leq Q \leq m$) n-TH($1 \leq n \leq N$) | (m-Q) k-TH($1 \leq k \leq n-1$) | n-TH($1 \leq n \leq N$) | n-TH(Q-1) |
| 2 | P($1 \leq P \leq m$) n-TH($1 \leq n \leq N-1$) | (m-P) k-TH($1 \leq k \leq n-1$) | L-TH($n+1 \leq L \leq N$) | n-TH+P |
| 3 | | M k-TH($1 \leq k \leq m$) | n-TH($2 \leq n \leq N$) | n-TH+1 |

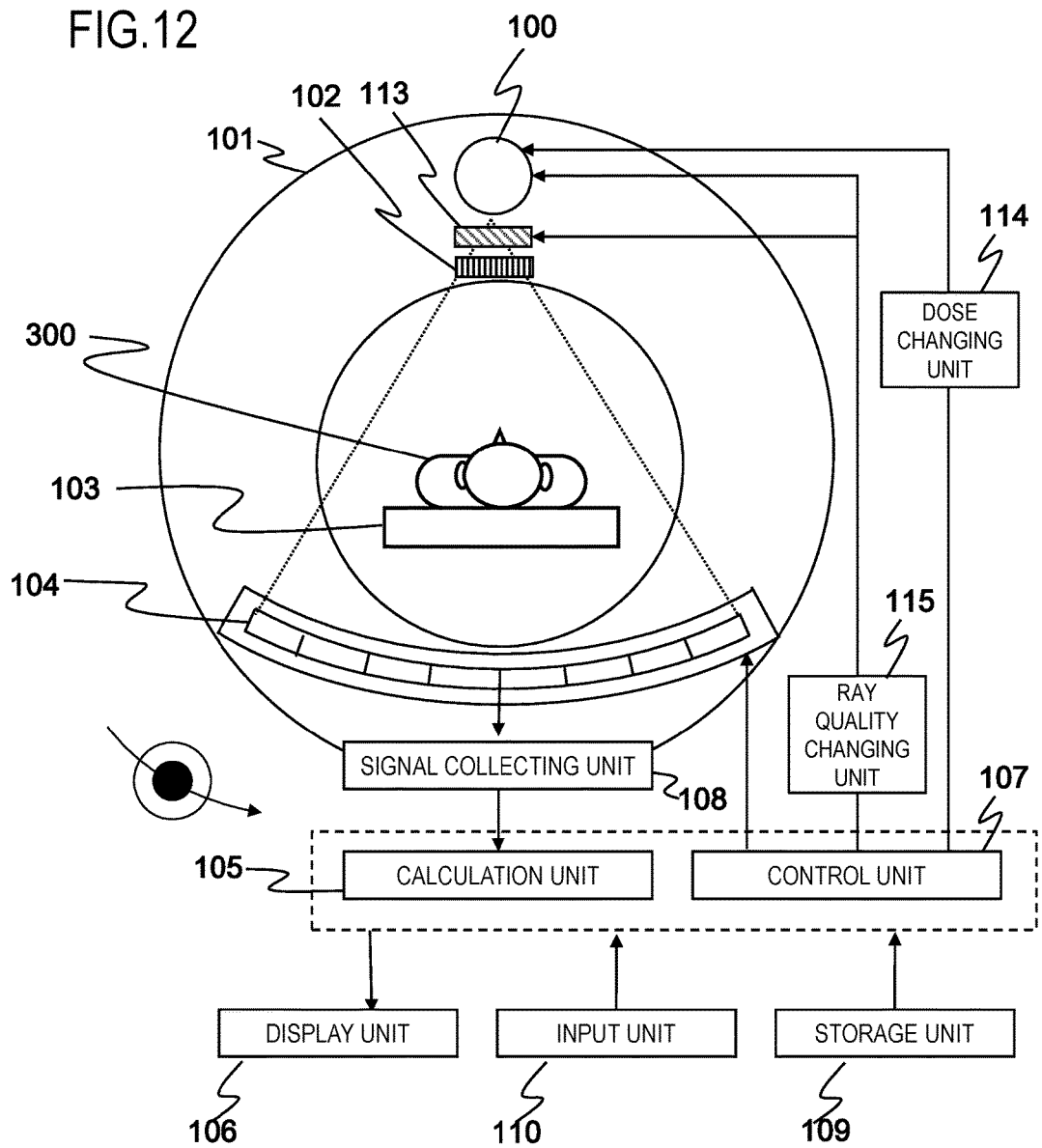

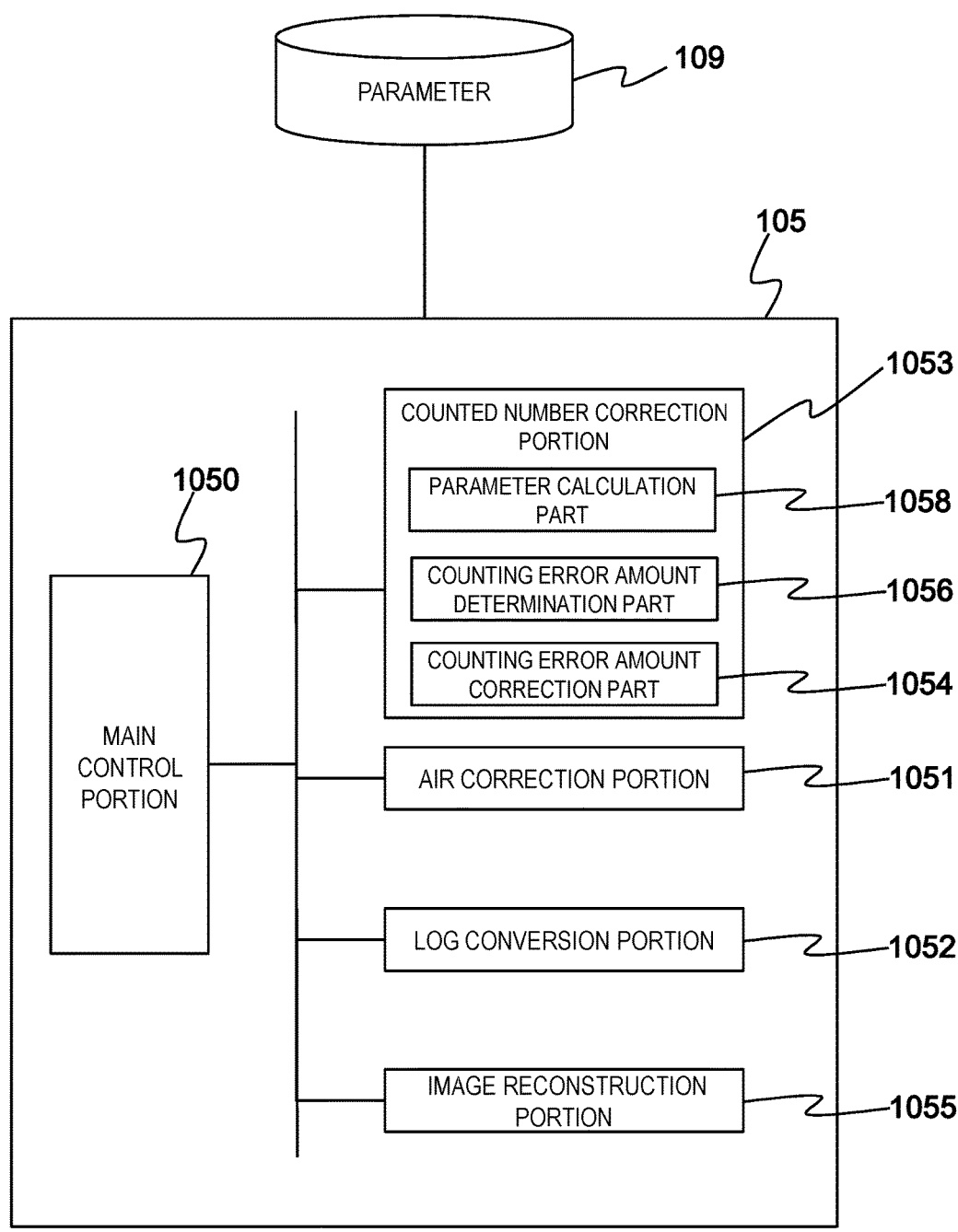

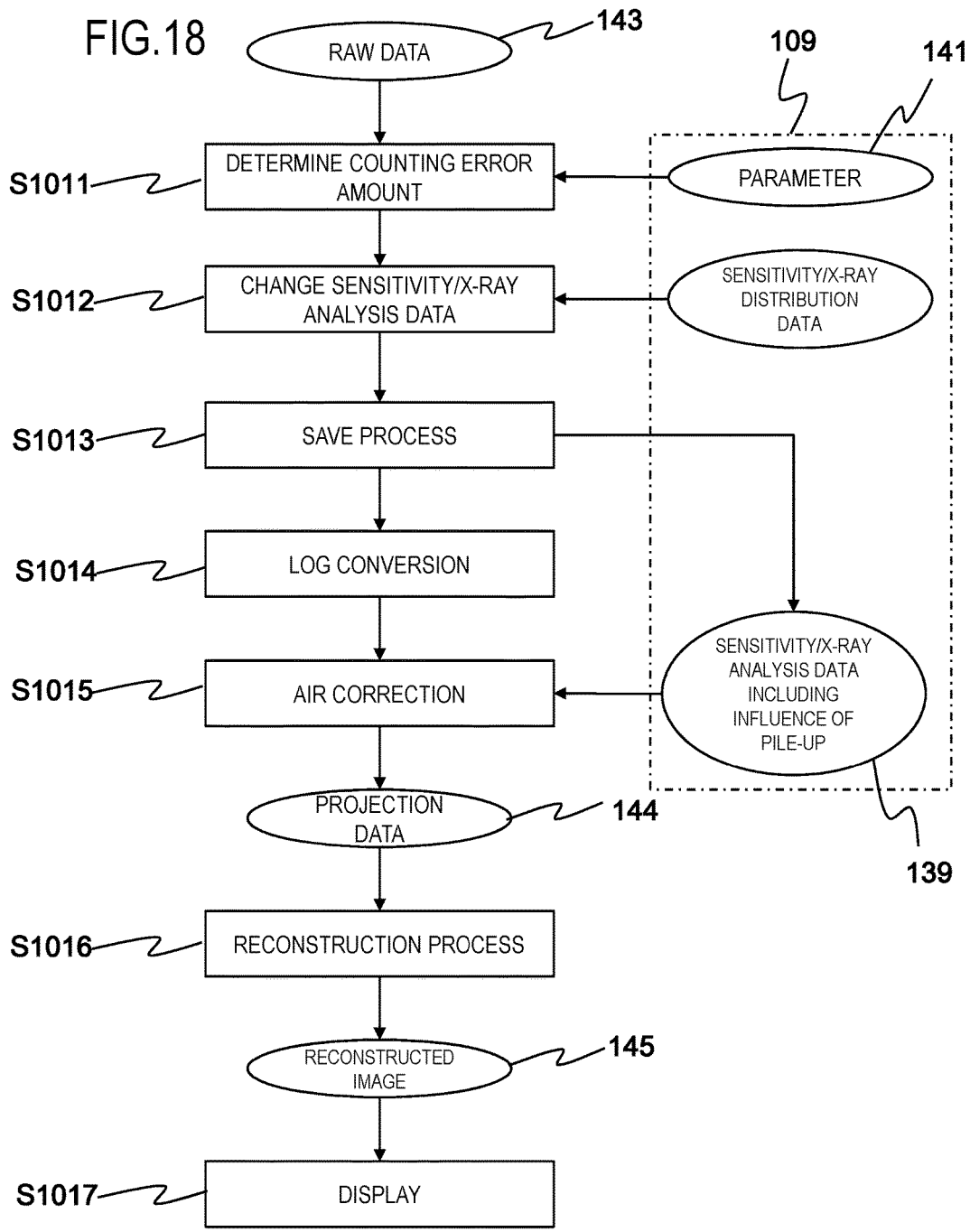

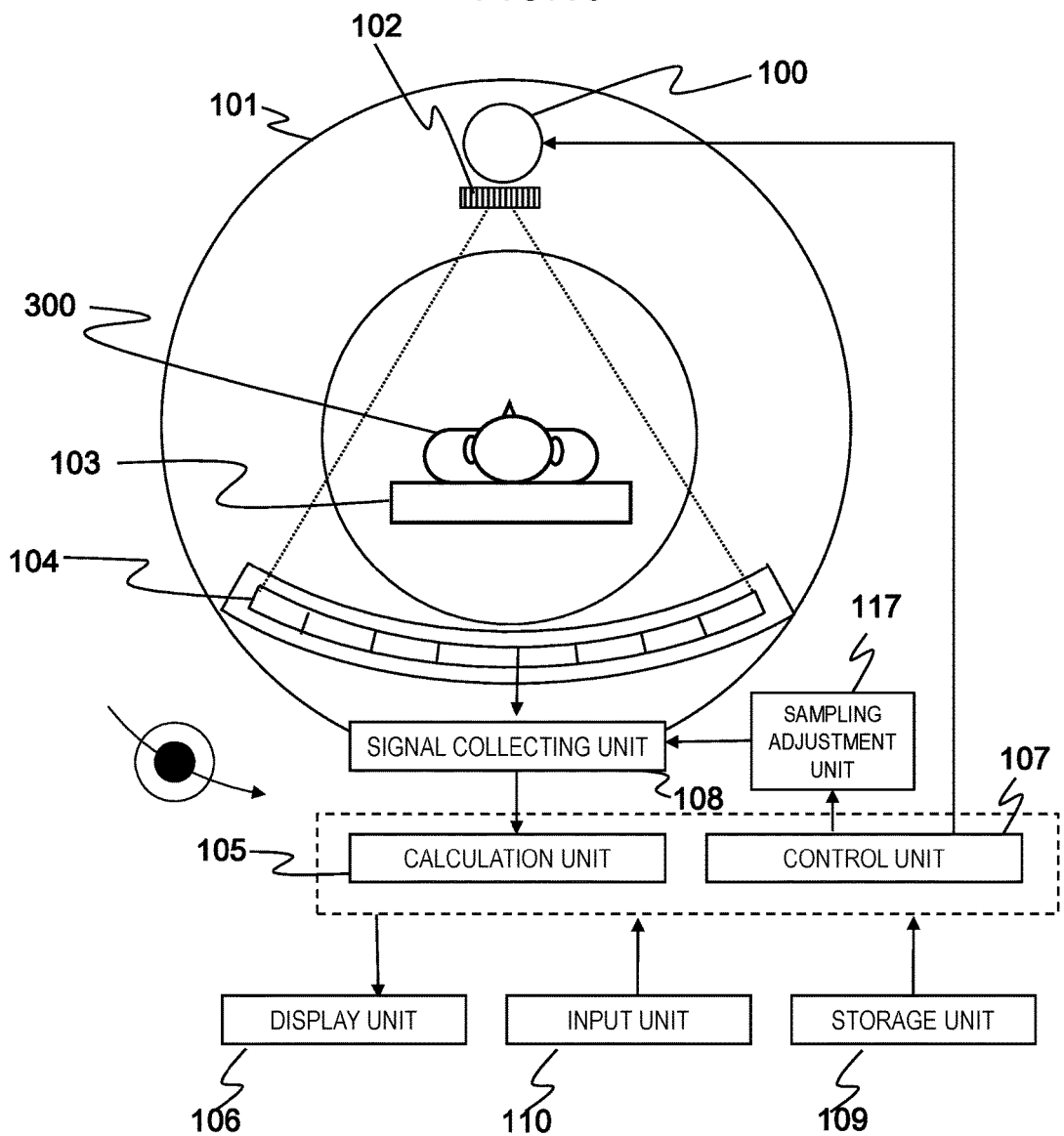

TUBE VOLTAGE
◉ 120kV ○ 140kV ○ 80kV ○ ......  — 171

TUBE VOLTAGE [ 200 ] mA  — 172

SCANNING PART
◉ CHEST ○ ABDOMEN ○ HEAD ○ ......  — 173

OBJECT
◉ ADULT ○ CHILD ○ ......  — 174

SAMPLING PERIOD OF TIME
◉ SHORT ○ LONG ○ ......  — 175

View TIME [ 1 ] ms  — 178

SCANNING TIME [ 1 ] SEC/ROTATION  — 179

NUMBER OF CAPTURED IMAGES [ 1000 ]  — 180

NUMBER OF ENERGY RANGES [ 3 ]  — 176
  FIRST ENERGY RANGE : 20eV - [ 70 ] KeV  — 177
  SECOND ENERGY RANGE : 70eV - [ 90 ] KeV  — 177
  THIRD ENERGY RANGE : 90eV - 120KeV

CONTRAST SCANNING ◉ YES ○ NO  — 181

TYPE OF CONTRAST AGENT
◉ IODINE ○ GOLD ○ ......  — 182

X-RAY IMAGING APPARATUS

TECHNICAL FIELD

The present invention relates to an image scanning apparatus such as an X-ray CT apparatus, and particularly to an X-ray scanning apparatus mounted with a photon counting type X-ray detector which classifies energy of incident X-ray photons into a plurality of energy ranges and counts the X-ray photons.

BACKGROUND ART

An X-ray CT apparatus is an apparatus which calculates an X-ray absorption coefficient on the basis of an X-ray transmission image (hereinafter, referred to as projection data) of an object obtained through scanning from a plurality of directions, and thus obtains a tomographic image (hereinafter, referred to as a reconstructed image) of the object, and is widely used in a medical field or a non-destructive inspection field.

A so-called integral X-ray detector is mounted in many current medical X-ray CT apparatuses, but, in recent years, an X-ray CT apparatus mounted with a photon counting type X-ray detector has been developed (for example, PTLs 1 and 2).

The X-ray detector includes an X-ray detection element having a detection layer of a semiconductor such as cadmium telluride (CdTe), and a reading circuit which classifies and obtains a digital signal for each energy range according to energy of incident X-ray photons. In this X-ray detector, if X-rays are incident to the X-ray detection element, first, electric charge corresponding to energy of X-ray photons is generated in the detection layer.

Next, the reading circuit reads the electric charge at a high speed at which each of the X-ray photons can be read, and classifies and counts the number of X-ray photons for each of several energy ranges according to energy of incident X-rays. In this case, the incident energy is identified by using an amount of generated electric charge.

The detection is similarly performed on each of a plurality of X-ray photons, the number of X-ray photons is counted in each energy range, and the counted number is converted into a digital signal. Through the measurement, projection data can be obtained for each energy range, and thus a reconstructed image can be obtained for each energy range by using the projection data. Energy information of an object can be obtained by using such projection data or a reconstructed image, and thus substance classifying performance can be improved.

In the photon counting type X-ray detector, in a case where a high dose of X-rays are incident per unit time, a plurality of X-ray photons may be incident during reading performed once. This phenomenon is called pile-up, a plurality of incident X-ray photons are counted as one, and energy thereof is detected as a wrong energy value. If the number of X-ray photons in each energy range is miscounted, accurate projection data cannot be obtained in each energy range. A reduction in quantitativeness of a CT value, deterioration in substance classifying performance, an artifact, and the like may occur in a reconstructed image created on the basis of the projection data.

In order to solve the pile-up problem, PTL 1 proposes a technique in which a preparation step of obtaining a correction coefficient for a counted number in each detection element is provided, and a measured counted number is corrected with the correction coefficient. PTL 2 discloses a technique in which, when incident energy is classified into respective energy ranges by using a predetermined threshold value, a threshold value for obtaining a correction value is set separately from an original threshold value, and a counted number in energy ranges defined by using this threshold value and a counted number in energy ranges defined by using the original threshold value are weight-added together so that a corrected counted number is obtained.

CITATION LIST

Patent Literature

PTL 1: Japanese Patent No. 2533717
PTL 2: Specification of U.S. Pat. No. 8,373,135

SUMMARY OF INVENTION

Technical Problem

Regarding causes of a counted number being inaccurate in a detection element, in addition to the above-described pile-up problem, there are causes such as a variation in a position or performance of the detection element, and deterioration in the performance. In the technique disclosed in PTL 1, a correction coefficient is calculated on the basis of a ratio between a counted number measured in a state in which incident energy is low by using an attenuation filter and a counted number measured by not using the attenuation filter, and a wrongly counted number due to various causes including pile-up can be corrected by using the correction coefficient. Depending on a cause of a wrongly counted number, for example, in a case of an error which depends on a position of a detection element, an algorithm for correcting the error is established, and thus the technique disclosed in PTL 1 cannot be applied to data having undergone the correction. Thus, a change in the number of pile-ups corresponding to a change in an X-ray spectrum due to an object cannot be estimated with high accuracy, and the accuracy of correcting the influence of the pile-up is low.

In the technique disclosed in PTL 2, a weight in a case where counted numbers in a plurality of energy ranges are subject to weighted addition is obtained through simulation, but the weight is determined depending on a size of a detection element or a conversion material, and correction is performed without taking into consideration interaction between X-ray photons in each energy range. As a result, correction specialized for pile-up is not performed.

Thus, as in the technique disclosed in PTL 1, a change in the number of pile-ups corresponding to a change in an X-ray spectrum due to an object cannot be estimated with high accuracy, and the accuracy of correcting the influence of the pile-up is low.

An object of the present invention is to perform correction of a counted number specialized for pile-up with high accuracy in an X-ray scanning apparatus including a photon counting type X-ray detection element.

Solution to Problem

According to the present invention, focusing on the fact that pile-up is related to two or more X-ray photons, and a counting error amount in a counted number due to pile-up is determined according to a pile-up occurrence probability in two or more X-ray photons. Specifically, a counting error correction technique with high accuracy is provided by employing a combination of energy ranges in which piled-up two or more X-ray photons are included, and an algorithm which is derived on the basis of an analysis result of a counting error in a counted number in each energy range due to a single pile-up.

Advantageous Effects of Invention

It is possible to perform correction of a counted number specialized for pile-up, and thus to prevent deterioration in classifying performance, a reduction in quantitativeness of a CT value, generation of an artifact, and the like caused by a counting error due to the pile-up.

BRIEF DESCRIPTION OF DRAWINGS

FIG. 8 is a diagram illustrating a change in a counted number due to pile-up of two X-ray photons as a table.

FIG. 9 is a diagram illustrating a change in a counted number due to pile-up of three X-ray photons as a table.

FIGS. 11(a) and 11(b) are diagrams illustrating a change in a counted number due to pile-up of two X-ray photons and a change in a counted number due to pile-up of three X-ray photons as tables in an X-ray CT apparatus of a second embodiment.

FIG. 12 is a schematic diagram illustrating a configuration of an X-ray CT apparatus of a third embodiment.

FIG. 13 is a functional block diagram mainly illustrating a configuration of a calculation unit in the third embodiment.

FIG. 18 is a diagram illustrating a flow of a correction process performed by an X-ray CT apparatus of the sixth embodiment.

FIG. 19 is a functional block diagram mainly illustrating a configuration of a control unit in a seventh embodiment.

FIG. 20 is a diagram illustrating an example of a user interface of an X-ray CT apparatus of the seventh embodiment.

DESCRIPTION OF EMBODIMENTS

Figure 1:
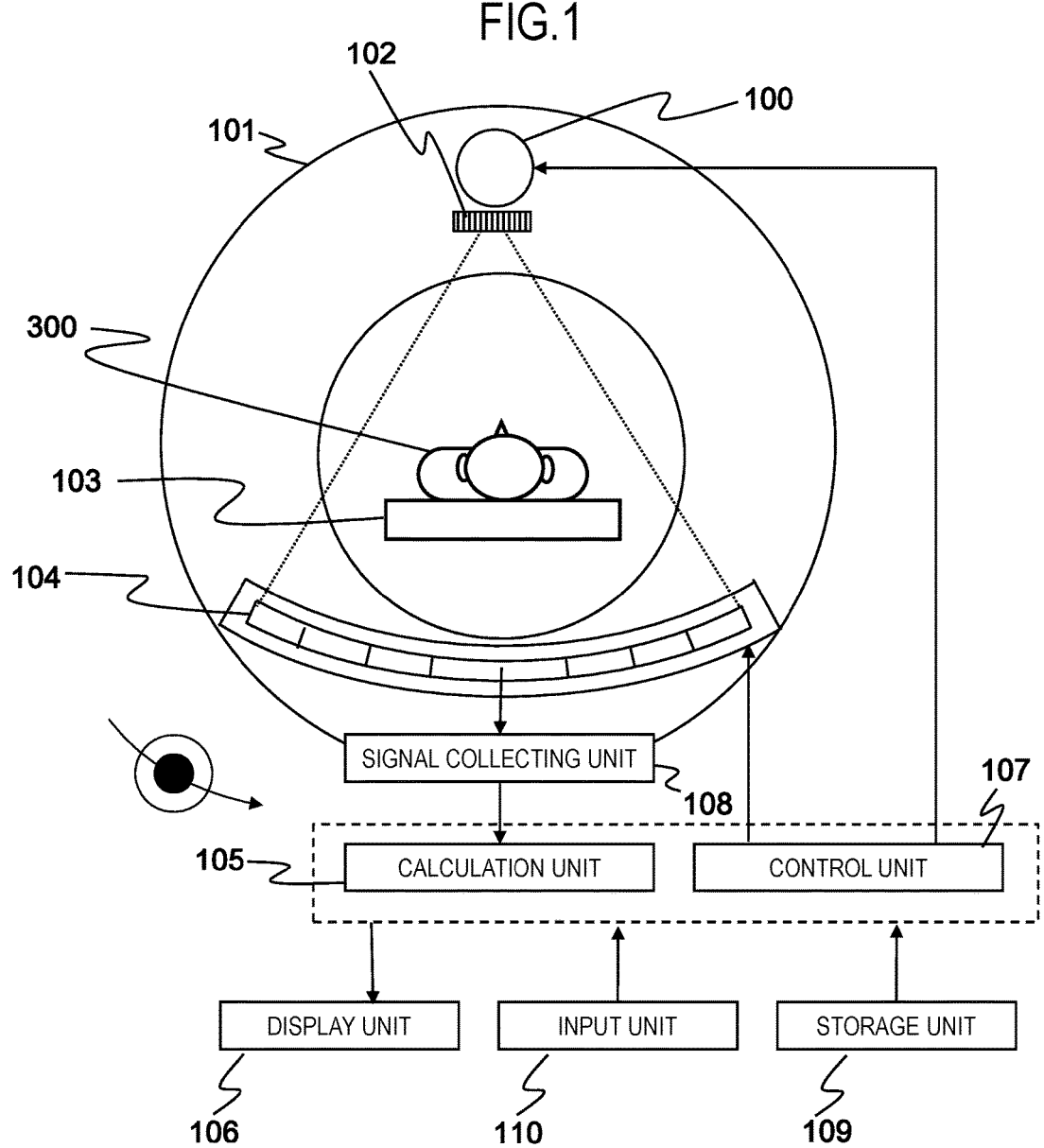
FIG. 1 is a schematic diagram illustrating an X-ray CT apparatus as an embodiment of an X-ray scanning apparatus of the present invention.

A description will be made of embodiments in which an X-ray scanning apparatus of the present invention is applied to an X-ray CT apparatus.

According to the present embodiment, there is provided an X-ray scanning apparatus including an X-ray detector (104) in which a plurality of photon counting type X-ray detection elements (400) are disposed, each of the X-ray detection elements detecting an incident X-ray photon, classifying energy of the X-ray photon into two or more energy ranges, and counting the X-ray photon; a signal collecting unit (108) that collects a counted number in the X-ray detection element; a correction unit (105, and 1051 to 1053) that corrects the counted number in the X-ray detection element and creates projection data; and an image reconstruction portion (1055) that performs reconstruction calculation on the projection data so as to create a reconstructed image, in which the correction unit (105) includes a counting error amount determination part (1056) that determines a counting error amount in a counted number due to pile-up according to a a pile-up occurrence probability in two or more X-ray photons.

The pile-up occurrence probability is determined, for example, by using a product of counted numbers measured in energy ranges in which two or more X-ray photons related to a single pile-up are respectively included.

The counting error amount determination part may determine the counting error amount on the basis of a product of a change amount of the counted number due to a single pile-up and the pile-up occurrence probability. Alternatively, the counting error amount determination part may determine the counting error amount by using a characteristic function including a product term of the counted numbers.

Hereinafter, with reference to the drawings, a configuration and an operation of an X-ray CT apparatus of the present embodiment will be described.

As illustrated in FIG. 1, the X-ray CT apparatus of the present embodiment includes, as a scanning system, an X-ray source 100, X-ray detectors 104 which is disposed an irradiation range of X-rays which are applied from the X-ray source 100, and a gantry rotation unit 101 which is disposed to oppose the X-ray source 100 and the X-ray detectors 104 and is rotated centering on a predetermined rotation axis. An X-ray collimator 102 which controls an irradiation range of X-rays is disposed near the X-ray source 100. An opening into which an object 300 is inserted is provided at the center of the gantry rotation unit 101, and a bed top plate 103 on which the object 300 lies is disposed in the opening. The bed top plate 103 and the gantry rotation unit 101 are configured to be relatively movable in predetermined directions.

The X-ray CT apparatus includes a control system controlling the scanning system, and also includes a control unit 107, a signal collecting unit 108, a calculation unit 105, a display unit 106, an input unit 110, and a storage device 109, and the like, as a signal processing system which processes a signal acquired by the X-ray detectors 104 according to an operation of the scanning system.

The control unit 107 is formed of an X-ray control portion which controls an operation of a generation driving source of the X-ray source 100, a reading control portion which controls a signal reading operation of the X-ray detectors 104, a scanning control portion which controls rotation of the gantry rotation unit 101 and movement of the bed top plate 103, and a general control portion which controls all of the above-described elements.

A part or a whole of each of the control unit 107 and the calculation unit 105 may be built as a system including a central processing unit (CPU), a memory, and the storage unit 109, and a function of each portion forming the control unit 107 and the calculation unit 105 may be realized by the CPU loading a program stored in a storage device in advance to the memory and executing the program. Some functions may be realized by using hardware such as an application specific integrated circuit (ASIC) or a field programmable gate array (FPGA).

Unless particularly mentioned, constituent elements of the scanning system, the control system, and the signal processing system have the same configurations as those of constituent elements of the known X-ray CT apparatus and also have the same functions.

A plurality of X-ray detectors 104 are disposed in an arc shape substantially centering on the X-ray source 100, and is rotated while maintaining a positional relationship with the X-ray source 100 due to rotation of the gantry rotation unit 101. For simplification of description, FIG. 1 illustrates a case where the number of X-ray detectors 104 is eight, but is forty, for example, in an actual apparatus. X-ray grids (not illustrated) are provided in front of the X-ray detectors 104, and prevent X-rays scattered by an object 300 or the like among X-rays applied from the X-ray source 100, from being incident to the X-ray detectors 104.

Figure 2:
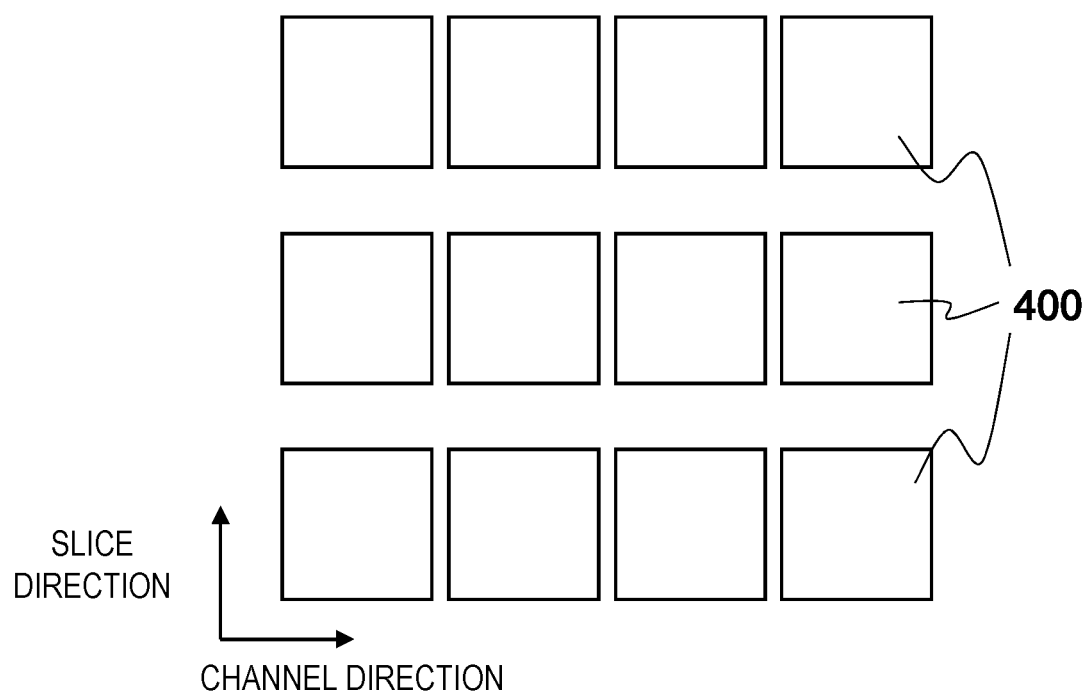
FIG. 2 is a diagram illustrating an example in which X-ray detection elements are disposed in an X-ray detector of the X-ray CT apparatus illustrated in FIG. 1.

Each of the X-ray detectors 104 has a structure in which a plurality of photon counting type X-ray detection elements 400 are disposed in a two-dimensional manner in a channel direction and a slice direction, for example, as illustrated in FIG. 2. FIG. 2 illustrates some X-ray detection elements 400 disposed in the X-ray detector 104, and illustrates that four X-ray detection elements in the channel direction and three X-ray detection elements in the slice direction are cut out. The X-ray detection elements 400 are disposed so that the channel direction matches a rotation direction, and the slice direction matches a rotation axis direction.

Figure 3:
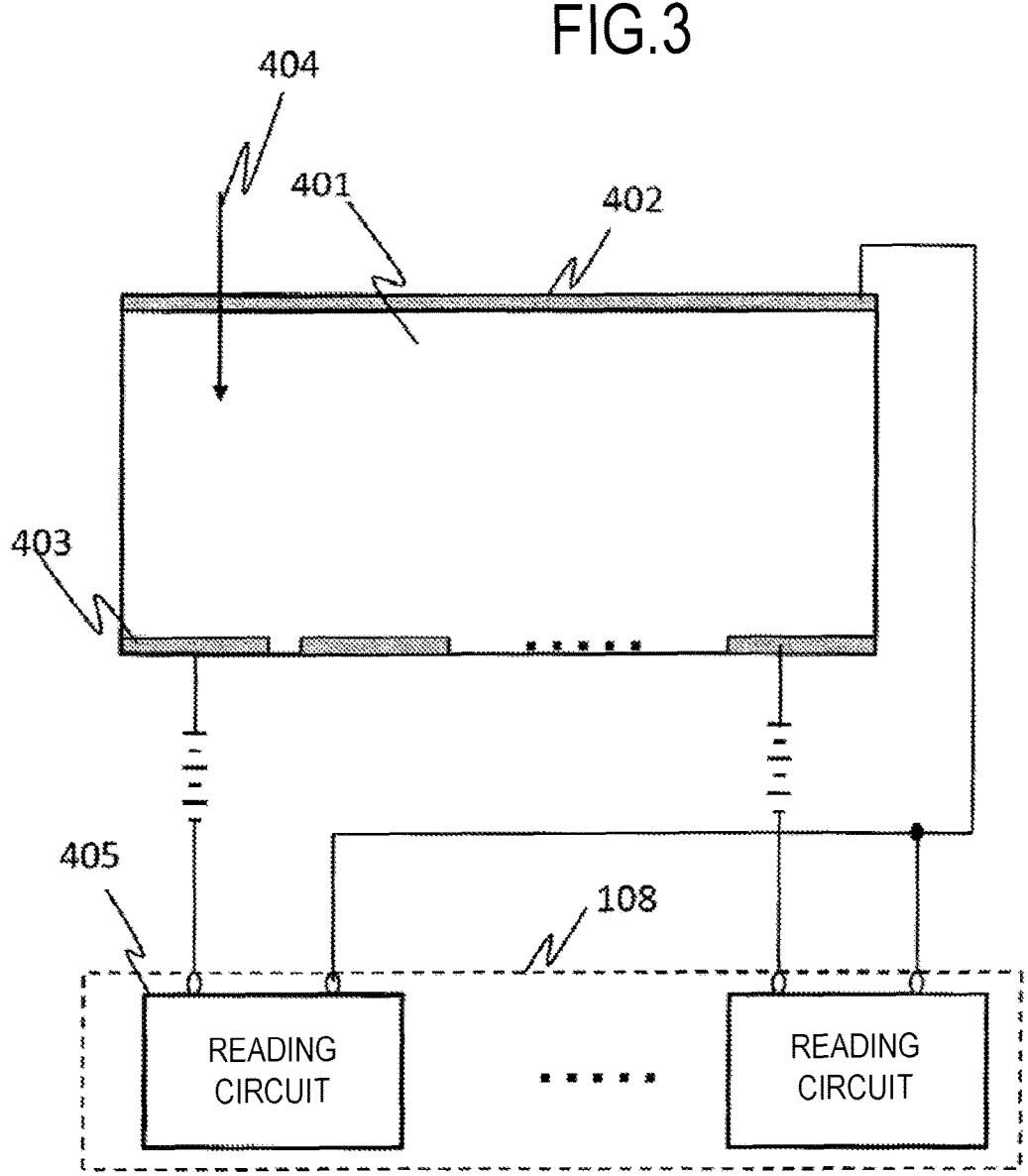
FIG. 3 is a diagram illustrating a schematic configuration of a photon counting type X-ray detection element.

Each of the X-ray detection elements 400 has a structure in which positive and negative electrodes 402 and 403 are disposed with a detection layer 401 interposed therebetween, and a reading circuit 405 is connected to the electrodes, as illustrated in FIG. 3. In the present embodiment, the negative electrode 402 is used in common to the respective X-ray detection elements 400, and an X-ray is incident to the detection layer 401 from the negative electrode 402 side as indicated by an arrow 404.

The detection layer 401 is made of a semiconductor material such as cadmium telluride (CdTe), cadminum zince telluride (CdZnTe), or silicon (Si), and detects an incident X-ray photon so as to generate electric charge with an amount corresponding to energy of the X-ray photon. The reading circuit 405 reads the electric charge generated by the detection layer 401 at a predetermined sampling interval, and classifies energy of the incident X-ray photon into a plurality of energy ranges on the basis of a predetermined threshold value by using an electric signal based on the electric charge.

For example, if there are two energy ranges, it is determined whether energy is included in an energy range (hereinafter, referred to as a low energy range) which is less than the predetermined threshold value, or an energy range (hereinafter, referred to as a high energy range) which is equal to or more than the predetermined threshold value. This determination is performed whenever sampling is performed, and energy of X-ray photons is classified into a high energy range and a low energy range when the X-ray photons are incident so that the number of X-ray photons in each range is counted.

Figure 4:
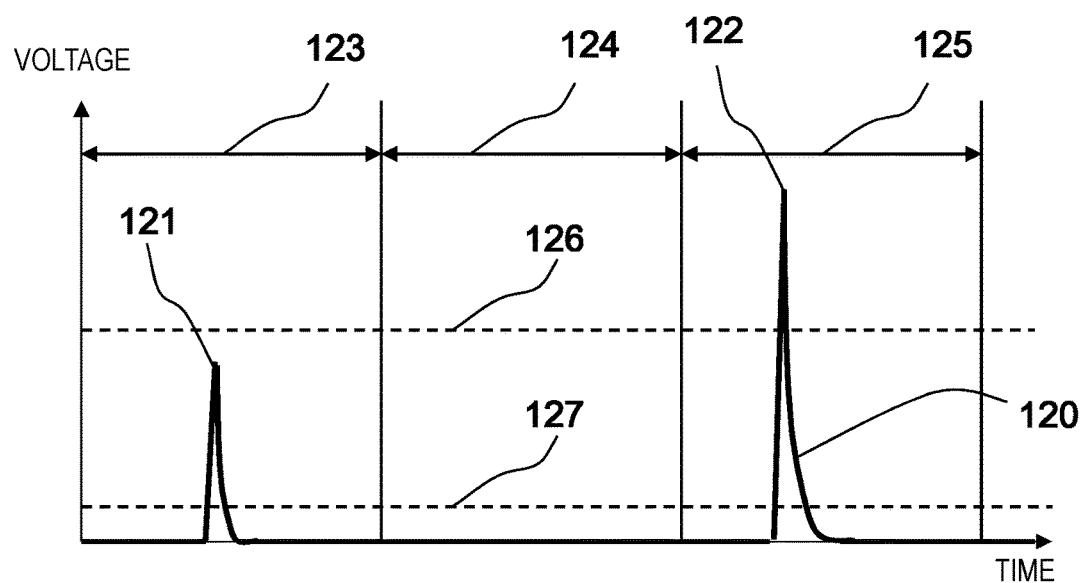
FIG. 4 is a diagram for explaining an energy classifying method performed by the X-ray detection element in FIG. 3.

A classifying method will be described with reference to FIG. 4. FIG. 4 is a graph illustrating a voltage 120 caused by generated electric charge, and a transverse axis expresses time, and a longitudinal axis expresses a voltage. In the illustrated example, an X-ray is incident so as to cause a pulse output 121 in a sampling period of time 123, and an X-ray is incident so as to cause a pulse output 122 in a sampling period of time 125. FIG. 4 illustrates a case where sampling is periodically performed not only at a timing of an X-ray being incident but also at a timing of an X-ray not being incident (a sampling period of time 124), but sampling may be performed at a timing of an X-ray photon being incident.

The reading circuit (FIG. 3, 405) compares the maximum value of an output voltage in the period with a threshold value 126 and a threshold value 127, and classifies the voltage, whenever sampling is performed. The threshold value 126 is used to classify an incident X-ray photon as a high energy range or a low energy range. The threshold value 127 is used to determine that no X-ray photon is incident. Here, the output voltage 120 changes due to circuit noise of the X-ray detectors 104 even when an X-ray is not input.

Therefore, in order to prevent this from being wrongly detected as a signal based on an X-ray, a value greater than zero is required to be set as the threshold value 127. Such threshold values are used, and, for example, in the sampling period of time 124 in FIG. 4, the output voltage 120 is equal to or less than the threshold value 127, and thus it is determined that no X-ray photon is input. In the sampling period of time 125, the output voltage 120 is more than the threshold value 126, and thus it is determined that X-rays in a high energy range are incident. In the sampling period of time 123, the output voltage 120 is more than the threshold value 127 but is equal to or less than the threshold value 126, and thus it is determined that X-rays in a low energy range are incident. In the above-described way, classification of the presence or absence of incidence and an energy range is performed.

Instead of performing classification using the maximum value in sampling, for example, an integral value of output voltage during sampling may be used, and a classification technique is not limited to the above-described technique.

Figure 5:
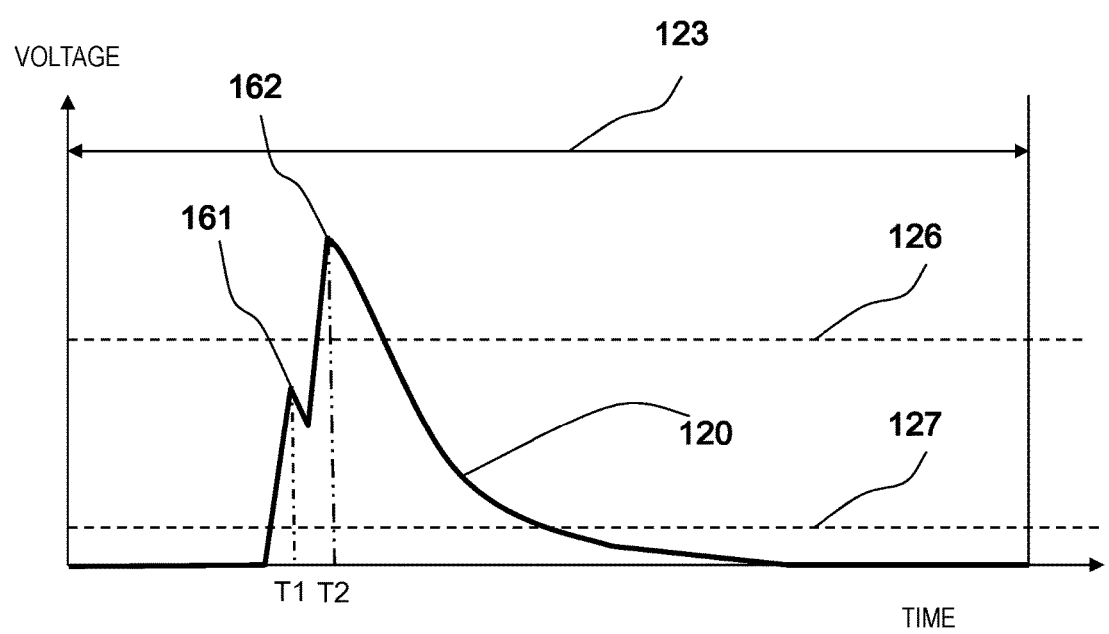
FIG. 5 is a diagram for explaining pile-up.

Here, in a case where two X-ray photons are incident in a single sampling period of time, the X-rays are not classified, and are thus counted as a single X-ray photon. For example, as illustrated in FIG. 5, a pulse output 161 caused by an X-ray photon in a low energy range and a pulse output 162 caused by an X-ray photon in a high energy range are counted by the reading circuit in a single sampling period of time 123, and the X-ray photon in the low energy range is not counted. This phenomenon is called pile-up, and causes wrong counting (counting error). The counting error caused by the pile-up is corrected by the calculation unit 105.

A general scanning operation of the X-ray CT apparatus will be described by exemplifying a case where two energy ranges are provided, on the basis of the above-described configuration.

First, if starting of actual scanning is input from the input unit 110, the control unit 107 controls application of X-rays from the X-ray source 100 and the gantry rotation unit 101 so as to start scanning. X-rays applied from the X-ray source 100 undergo restriction of an irradiation field in the X-ray collimator 102 so as to be applied to the object 300 placed on the bed top plate 103, and X-rays transmitted through the object 300 are detected by the X-ray detectors 104. The X-ray detectors 104 classify energy of the incident X-rays into a high energy range and a low energy range as described above. This classification is performed during one view for a predetermined number of times of sampling, and the number of incident X-ray photons in the high energy range and the low energy range are counted. The signal collecting unit 108 converts a signal corresponding to each number of X-ray photons into a digital signal, and outputs the signal as a counted number in each energy range.

The control unit 107 repeatedly performs this scanning while changing an irradiation angle of X-rays with respect to the object 300 by rotating the gantry rotation unit 101 in the rotation direction, and acquires digital signals (hereinafter, referred to as raw data) corresponding to 360 degrees. The scanning is performed during a plurality of views, for example, every 0.4 degrees. During that time, an X-ray irradiation position is controlled as necessary.

Next, the calculation unit 105 performs a predetermined correction process on the raw data collected by the signal collecting unit 108, so as to create projection data. The calculation unit 105 performs reconstruction on the projection data so as to create a reconstructed image of an X-ray absorbance coefficient distribution of the object 300, for example, in each of the high energy range and the low energy range. Results thereof are displayed on the display unit 106.

The correction process performed by the calculation unit 105 includes not only well-known air correction and LOG conversion, but also counted number correction of correcting an error in a counted number caused by pile-up of X-ray photons which is incident to the X-ray detection element.

Hereinafter, a description will be made of embodiments of correction processes performed by the calculation unit 105.

First Embodiment

An X-ray CT apparatus of a first embodiment estimates a counting error amount in each energy range caused by pile-up on the basis of a product of a pile-up occurrence probability and a change number in each energy range when pile-up occurs.

A counting error amount determination part (1056) of the present embodiment may determine a decrease amount (counting omission amount) due to a single pile-up in a counting error amount in a single energy range by using a counted number measured in the single energy range and a counted number measured in energy ranges other than the single energy range. An increase amount (counting redundancy amount) due to a single pile-up in a counting error amount in a single energy range may be determined by using a counted number measured in an energy range lower than the single energy range.

The X-ray CT apparatus of the present embodiment includes a storage unit (109) storing a parameter including information regarding a change amount caused by a single pile-up, the counting error amount determination part (1056) may determine a counting error amount by using the parameter stored in the storage unit and counted numbers measured in energy ranges in which two or more piled-up X-ray photons are respectively included.

Figure 6:
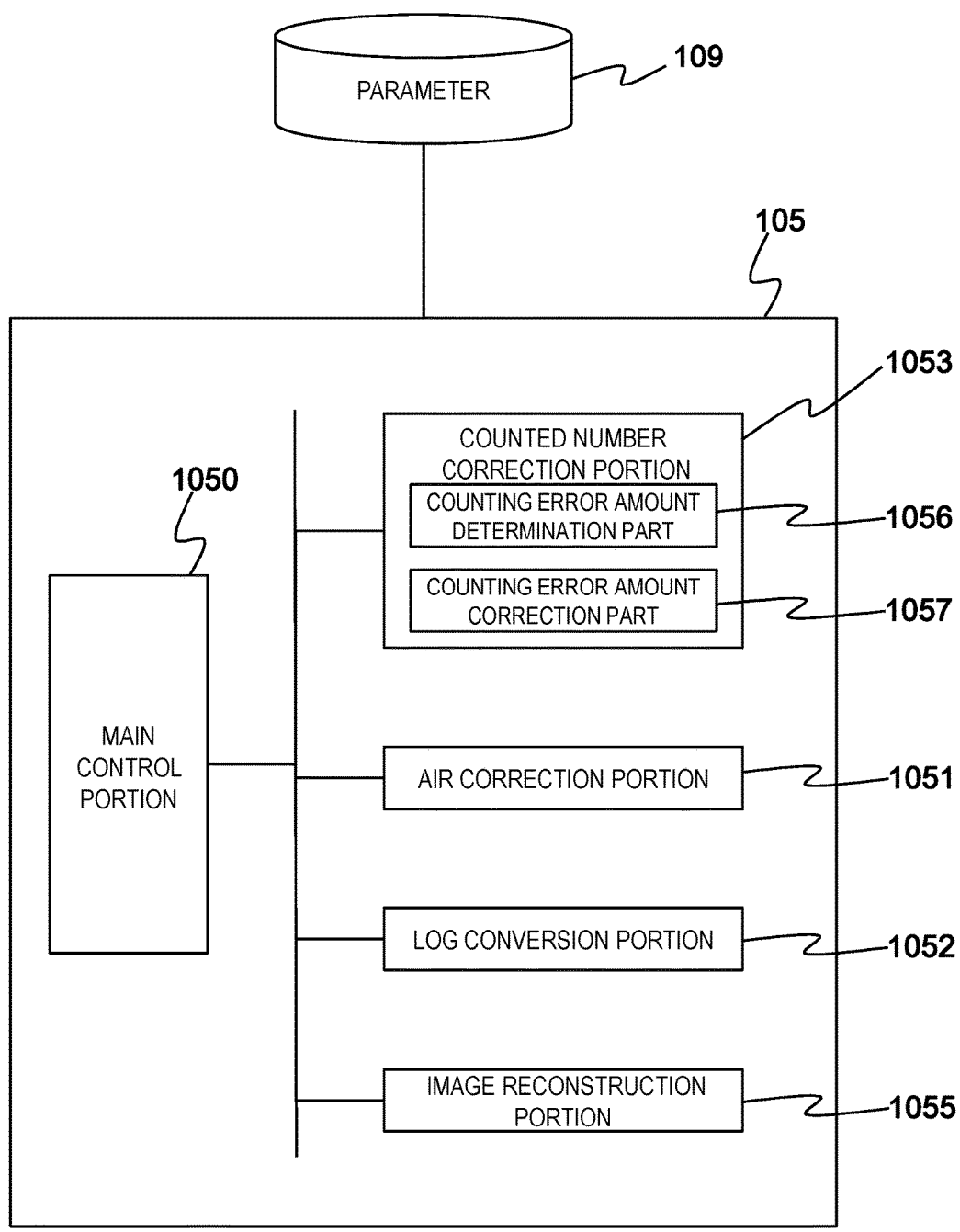
FIG. 6 is a functional block diagram mainly illustrating a configuration of a calculation unit in a first embodiment.

FIG. 6 illustrates a configuration of the calculation unit 105 of the X-ray CT apparatus of the present embodiment. As illustrated in FIG. 6, the calculation unit 105 includes a main control portion 1050, an air correction portion 1051, a LOG conversion portion 1052, a counted number correction portion 1053, and an image reconstruction portion 1055. The air correction portion 1051, the LOG conversion portion 1052, and the counted number correction portion 1053 form a correction unit which performs necessary correction on raw data. The counted number correction portion 1053 includes a counting error amount determination part 1056 which determines a counting error amount included in raw data, a counting error amount correction part 1057 which corrects the raw data by using the counting error amount determined by the counting error amount determination part 1056, and the like. The correction unit and the image reconstruction portion 1055 are operated under the control of the main control portion 1050.

A parameter or data used for computation in the calculation unit 105 is saved in the storage unit 109, and the calculation unit 105 performs computation for correction or image reconstruction by reading the parameter or the like from the storage unit 109 as necessary. The parameter or the data includes, for example, an X-ray sensitivity distribution or an X-ray distribution used by the air correction portion 1051, and a parameter or a function used to determine a counting error amount in the counted number correction portion 1053.

Next, a description will be made of a correction process performed by the calculation unit 105 with reference to a flow illustrated in FIG. 7.

Figure 7:
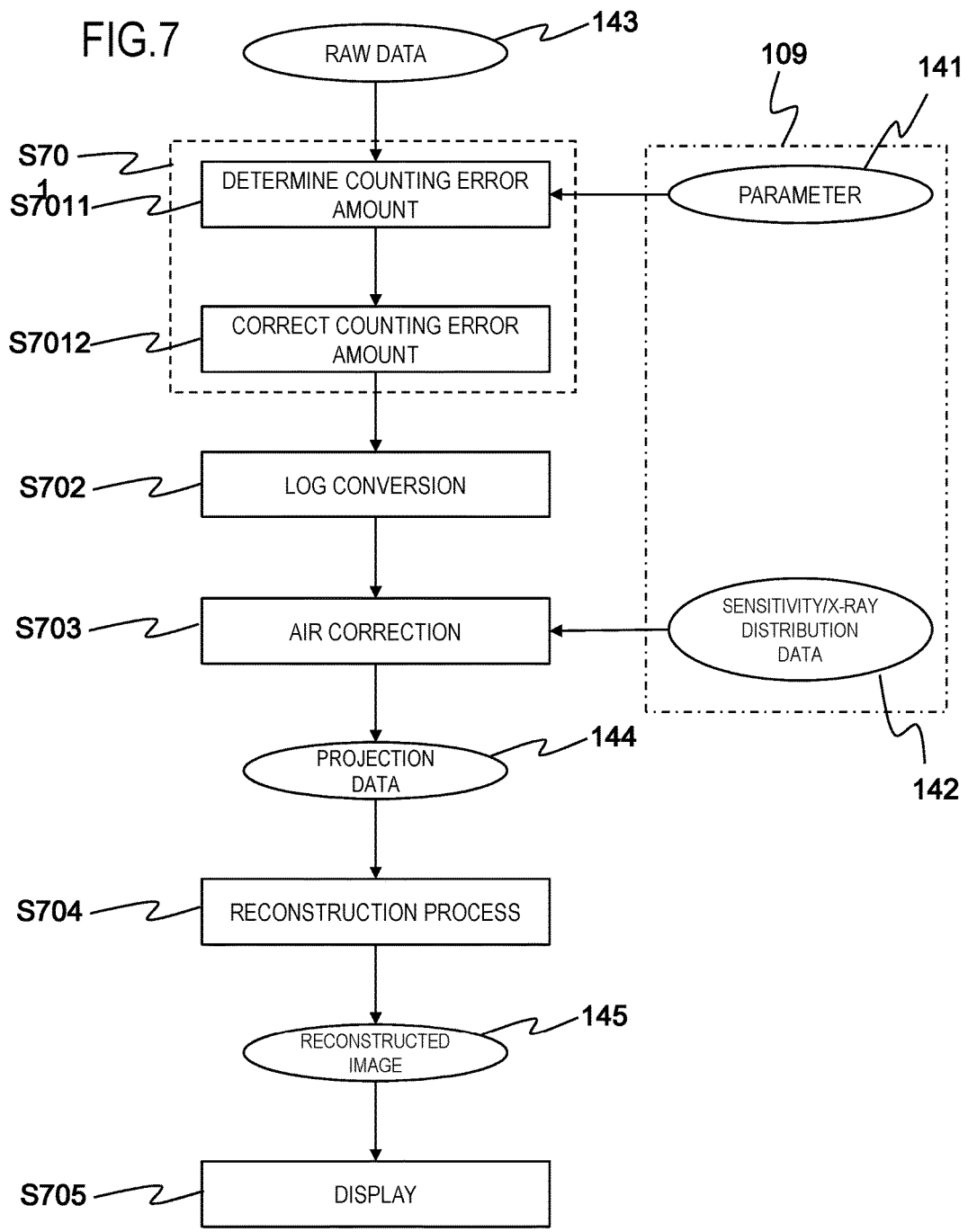
FIG. 7 is a diagram illustrating an example of a flow of a correction process performed by an X-ray CT apparatus of the first embodiment.

As illustrated in FIG. 7, the calculation unit 105 performs counted number correction (S701) on raw data 143 received from the signal collecting unit 108. Here, a difference between the number of incident X-ray photons and a counted number which is measured, caused by pile-up or the like, is corrected. At this time, parameters 141 stored in the storage unit 109 are read, and calculation for the correction process is performed. Details thereof will be described later.

Next, LOG conversion (S702) is performed. In the LOG conversion, if a value before being converted is indicated by X, and a value after being converted is indicated by Y, for example, conversion is performed according to Equation (1). Here, a and b are constant coefficients.

[Equation 1]

$$Y = a\ \mathrm{LOG}(X) + b \qquad (1)$$

Next, air correction (S703) is performed. This correction is performed by subtracting sensitivity/X-ray distribution data 142 which is measured prior to main scanning and is created to be saved in the storage unit 109, from raw data having undergone the LOG conversion. The sensitivity/X-ray distribution data 142 is created for each energy range. Regarding a creation method, for example, the raw data 143 based on energy is acquired by applying X-rays from the X-ray tube 100 without the object 300, counted number correction (S701) is performed on the raw data, addition averaging is performed in a view direction for each X-ray detection element 400, normalization is performed by using an average value of outputs from the X-ray detectors 104, and LOG conversion is performed for creating the sensitivity/X-ray distribution data.

Projection data 144 is obtained through the above-described process, and a reconstructed image 145 is created by performing a reconstruction process (S704). Finally, the reconstructed image 145 is displayed on the display unit 106 (S705).

In FIG. 7, a description has been made of an example in which the counted number correction (S701) is performed on the raw data 143, and then the air correction (S703) is performed, but the correction process illustrated in FIG. 7 is only an example, and does not limit the present invention. For example, a correction order may differ by performing count correction after air correction is performed. Count correction may be performed along with other processes. Other corrections may be added, or air correction may be omitted.

Next, a specific process in the counted number correction (S701) will be described in detail. The process is formed of a process (S7011) performed by the counting error amount determination part 1056 and a process (S7012) performed by the counting error amount correction part 1057.

The counting error amount determination process (S7011) is a process in which a counting error amount caused by counting omission or counting redundancy due to pile-up is estimated by using counted numbers in both of the energy ranges. In the following description, the description will be made of a case where correction is performed by taking into consideration both a counting omission amount and a counting redundancy amount as a counting error amount, but this is only an example, and correction may be performed by taking into consideration only one thereof.

The counting error amount correction process (S7012) is a process in which correction is performed by subtracting the counting error amount determined in the counting error amount determination process (S7011) from the raw data 143 received from the signal collecting unit 108 in actual scanning. Consequently, the influence of a counting error due to pile-up is removed.

In the counting error amount determination process (S7011), a counting error amount is estimated on the basis of a product of a pile-up occurrence probability and a change number in each energy range when pile-up occurs. The pile-up occurrence probability is computed by using a counted number in an energy range. The counting error amount is estimated in a state of being divided into counting omission showing a negative change number and counting redundancy showing a positive change number. The counting omission is estimated by using a counted number of X-ray photons in an energy range in which a counting error amount is determined and counted numbers of X-ray photons in other energy ranges. The counting redundancy is estimated by using a counted number of X-ray photons in an energy range lower than the energy range in which a counting error amount is determined. The counting error amount determination part 1056 performs computation for estimation for each energy range so as to determine the counting error amount.

A description of principles of a pile-up probability and a method of determining a change number will be made prior to description of a computation formula used for computation for estimation in the counting error amount determination part 1056.

The pile-up probability is a probability of two or more X-ray photons being simultaneously incident during sampling performed once, and is thus a product of probabilities of the respective X-ray photons being measured during sampling performed once. Since a probability of a single X-ray photon being measured during sampling performed once is proportional to the number of X-ray photons which is incident per unit time, a case where two or more X-ray photons are incident is proportional to a product of the numbers of X-ray photons which are incident per unit time for each of the incident X-ray photons.

Here, the number of X-ray photons is approximately the same as a counted number, and thus a pile-up probability is approximately proportional to a product of counted numbers of incident X-ray photons. Therefore, for example, a probability that pile-up may occur due to two X-ray photons such as an X-ray photon in a high energy range and an X-ray photon in a low energy range is proportional to a product of counted numbers in the high energy range and the low energy range.

On the other hand, a change number in each energy range when the pile-up occurs differs in a combination of energy ranges in which X-ray photons are simultaneously incident during sampling. FIG. 8 is a table collecting change numbers in each energy range when pile-up occurs due to two X-ray photons. As shown in this table, in a case where pile-up occurs due to an X-ray photon in a low energy range and an X-ray photon in a low energy range, an energy range in which the number of X-ray photons is counted may be both of a high energy range and a low energy range (Case 1 and Case 2).

On the other hand, in a combination (Case 3) of X-ray photons in a low energy range and a high energy range or a combination (Case 4) of X-ray photons in a high energy range and a high energy range, an X-ray photon is counted as an X-ray photon in a high energy range. This is because, in a case where pile-up occurs, an integral value or a wave height of a signal is more than that based on a single X-ray photon. When X-ray photons in a low energy range and a high energy range cause pile-up, of the low energy range and the high energy range, an energy range in which the X-ray photon is measured is determined stochastically depending on ray quality of the X-ray photon in each energy range.

As mentioned above, in a case where pile-up occurs due to two X-ray photons, the following change occurs.

[Case 1]: In a case where an X-ray photon in a low energy range and an X-ray photon in a low energy range cause pile-up, and thus the X-ray photons are measured as an X-ray photon in a single low energy range, a counted number in the low energy range is reduced by 1.

[Case 2]: In a case where an X-ray photon in a low energy range and an X-ray photon in a low energy range cause pile-up, and thus the X-ray photons are measured as an X-ray photon in a single high energy range, a counted number in the low energy range is reduced by 2, and a counted number in the high energy range is increased by 1.

[Case 3]: In a case where an X-ray photon in a low energy range and an X-ray photon in a high energy range cause pile-up, and thus the X-ray photons are measured as an X-ray photon in a single high energy range, a counted number in the low energy range is reduced by 1.

[Case 4]: In a case where an X-ray photon in a high energy range and an X-ray photon in a high energy range cause pile-up, and thus the X-ray photons are measured as an X-ray photon in a single high energy range, a counted number in the high energy range is reduced by 1.

If this change is considered, counting omission occurs when an X-ray photon in a certain energy range and X-ray photons in the certain energy range or in energy ranges other than the certain energy range cause pile-up, and counting redundancy occurs when X-ray photons in energy ranges lower than the certain energy range cause pile-up. Therefore, it can be seen that a counting omission amount can be estimated by using a counted number in a certain energy range and counted numbers in the certain energy range or in energy ranges other than the certain energy range, and a counting redundancy amount can be estimated by using counted numbers in energy ranges lower than the certain energy range.

From the above description, a counting error amount in an i-th (where i is an integer of 1 or more) X-ray detection element may be expressed as in the following Equations (2-1) and (2-2) in a case where an energy range is divided into two ranges.

[Equation 2]

if $n = 2$ (2 – 1)
$$B_n(i) = -a_{222}\varepsilon_{222}R_2(i)R_2(i) + b_{112}\varepsilon_{112}R_1(i)R_1(i)$$

if $n = 1$ (2 – 2)
$$B_n(i) = -a_{111}\varepsilon_{111}R_1(i)R_1(i) - a_{112}\varepsilon_{112}R_1(i)R_1(i) - a_{122}\varepsilon_{122}R_1(i)R_2(i)$$

In the equations, $B_n(i)$ indicates a counting error amount in an n-th (where n is 1 or 2) energy range, and $R_n(i)$ indicates a counted number in the n-th (where n is 1 or 2) energy range. Here, a low energy range is the first energy range, and a high energy range is the second energy range. In addition, $\varepsilon_{nhj}$ indicates a probability that, when two X-ray photons in the n-th and an h-th (where h is 1 or 2) energy ranges cause pile-up and are thus counted as an X-ray photon in a j-th (where j is an integer of h or more and n or more) energy range, and a decreasing number at this time is indicated by $a_{nhj}$, and an increasing number at this time is indicated by $b_{nhj}$. In a case where a counting error amount is positive, this indicates that a counted number is measured more due to pile-up, and, in a case where a counting error amount is negative, this indicates that a counted number is measured less.

The first term of the right side in Equation (2-1) (if n=2) indicates a decrease in [Case 4], and the second term thereof indicates an increase in [Case 2]. The first term of the right side in Equation (2-2) (if n=1) indicates a decrease in [Case 1], the second term thereof indicates a decrease in [Case 2], and the third term thereof indicates a decrease in [Case 3]. Therefore, the decrease amount $a_{nhi}$ becomes $a_{111}=1$, $a_{112}=2$, $a_{122}=1$, and $a_{222}=1$, and the decrease amount $b_{nhj}$ becomes $b_{112}=1$.

In a case (Case 3) where an X-ray photon in a low energy range and an X-ray photon in a high energy range cause pile-up, and a case (Case 4) where an X-ray photon in the high energy range and an X-ray photon in the high energy range cause pile-up, only the X-ray photon in the high energy range is counted, and thus $\varepsilon_{122}$ is the same as a probability that an X-ray photon in the low energy range and an X-ray photon in the high energy range may cause pile-up, and $\varepsilon_{222}$ is the same as a probability that two X-ray photons in the high energy range may cause pile-up. The two X-ray photons may be replaced with each other, and this leads to $\varepsilon_{nhj}=\varepsilon_{hnj}$. Equations (2-1) and (2-2) (hereinafter, collectively referred to as Equation (2) in some cases) do not discriminate both of the two expressions from each other (that is, one representative expression).

In Equation (2), if a product or a sum of the decrease amount $a_{nhj}$ and the probability $\varepsilon_{nhj}$ is indicated by a parameter $\alpha_{nh}$, and a product of the increase amount $b_{nhj}$ and the probability $\varepsilon_{nhj}$ is indicated by a parameter $\beta_{nh}$, the counting error amount $B_n(i)$ may be expressed as in Equations (3-1) and (3-2) (hereinafter, collectively referred to as Equation (3) in some cases).

[Equation 3]

if $n = 2$ (3-1)
$$B_n(i) = -\alpha_{nN}R_N(i)R_n(i) + \sum_{g=1}^{n-1}\sum_{h=g}^{n-1}\beta_{gh}R_g(i)R_j(i)$$

if $n = 1$ (3-2)
$$B_n(i) = -\sum_{h=1}^{N}\alpha_{hn}R_h(i)R_n(i)$$

In Equation (3), the first term having $\alpha_{hn}$ indicates a counting omission amount, and the second term having $\beta_{hn}$ indicates a counting redundancy amount. N indicates the number of energy ranges, and is an integer of 2 or more with the magnitude in a range which can be processed by the calculation unit. The letter g in $\beta_{gh}$ and $R_g$ indicates a g-th (where g is 1 or 2) energy range in the same manner as the letters n and h, and is used to be differentiated from the letters n and h.

$\varepsilon_{nhj}$ in Equation (2) or the parameters $\alpha_{hn}$ and $\beta_{hn}$ in Equation (3) may be obtained through simulation or test. In the present embodiment, a case where the parameters are determined through simulation will be described.

The simulation may be performed according to, for example, a Monte Carlo method by using a computer which is different from the X-ray CT apparatus. In the simulation, a dose (energy) and quality of X-rays generated from an X-ray source, and a simulated object are set, and an X-ray detection element model in which a wave height corresponding to energy of X-rays attenuates through subsequent attenuation is set. X-rays having predetermined ray quality is generated from the X-ray source, X-ray photons are transmitted through the simulated object so as to be incident to X-ray detection elements of an X-ray detector, and the incident X-rays (signals) are classified into energy ranges by a wave height whenever sampling is performed in the X-ray detection element. At this time, in a case where two or more X-ray photons are incident and cause pile-up, wave heights are superimposed on each other by taking into consideration timings as well.

A description will be made of an example of a case where pile-up occurs with reference to FIG. 5 described above. FIG. 5 illustrates an example of a case where X-ray photons in a low energy range are respectively incident at a time point T1 and a time point T2 in the sampling period of time 123. In this case, in an output voltage curve 120, since the other X-ray photon 162 is incident at the time point T2 before an output 161 caused by the X-ray photon which is incident at the time point T1 sufficiently falls, a peak of a wave height is measured at the time point T2, and thus it is measured that a single X-ray photon in a high energy range is incident.

As mentioned above, simulation is also performed by taking into consideration a case where pile-up occurs, and thus it is classified that a single X-ray photon having energy higher than that of an incident X-ray photon is incident in the same manner as in an actual case. Such simulation in which pile-up occurs is performed while changing an object, an X-ray dose, ray quality, or the like, and thus a classification result in each energy range is obtained.

On the other hand, similar simulation is performed, and a classification result in a case where X-rays having the same ray quality are measured by an ideal X-ray detector is obtained. Here, the ideal X-ray detector is a detector in which very short sampling is performed, and pile-up does not occur. The parameters $\alpha_{hn}$ and $\beta_{hn}$ can be determined by comparing the classification results with each other. The parameters $\alpha_{hn}$ and $\beta_{hn}$ determined in the above-described way are saved in the storage unit 109 as the parameters 141.

As described above, in the counting error amount determination process (S7011), the counting error amount $B_n(i)$ may be determined by using Equation (2) or Equation (3).

Next, in counting error amount correction (S7012), input and output characteristics are corrected by using the counting error amount $B_n(i)$ calculated in the process (S7011). Here, for example, a corrected counted number is calculated by subtracting the obtained counting error amount $B_n(i)$ from the measured counted number, and thus correction is performed. Consequently, a counting error in the number of X-ray photons in each energy range due to pile-up can be corrected. The above-described processes (S7011 and S7012) are performed on all X-ray detection elements (i in all cases), and thus corrected projection data can be obtained.

In Equation (2) or Equation (3), a counted number before a counting error amount is corrected is used as a counted number ($R_n(i)$) in each energy range in order to calculate a pile-up occurrence probability, but is an approximate value, and is suitable, for example, when the influence of pile-up is not great. On the other hand, when the influence of pile-up is great, it is preferable to use a counted number after a counting error amount is corrected by removing the influence of pile-up. In this case, successive processes may be performed in order to prevent a computation time from increasing due to a computation process in the counted number correction (S701) being complex. In other words, for example, first, the counting error amount determination process (S7011) is performed by using a counted number before a counting error amount is corrected, and a value is calculated by performing the counting error amount correction process (S7012) by using a determined counting error amount. The processes (S7011 and S7012) are repeatedly performed by using this value, and thus a counting error amount is determined. The number of times of repetition is determined as appropriate on the basis of a trade-off relationship between desired accuracy and computation time.

In Equations (2) and (3), only pile-up of two X-ray photons having a high pile-up occurrence probability is taken into consideration, but, if an X-ray dose is high, pile-up of three or more X-ray photons increases, and thus there may be a case of not being negligible.

Hereinafter, a description will be made of a correction process (S701) in a case where pile-up occurs due to three or more X-ray photons. Also in this case, in the same manner as in a case of pile-up of two X-ray photons, a counting error amount in pile-up of three or more X-ray photons is estimated on the basis of a product of a pile-up occurrence probability and a change number in each energy range when pile-up occurs.

The pile-up occurrence probability is calculated, for example, by using a counted number of X-ray photons in an energy range. The counting omission is estimated by using a counted number of X-ray photons in an energy range in which a counting error amount is determined and counted numbers of X-ray photons in other energy ranges, and the counting redundancy is estimated by using a counted number of X-ray photons in an energy range lower than the energy range in which a counting error amount is determined.

In a case where pile-up occurs due to m (where m is an integer of 3 or more) X-ray photons, the following change occurs depending on a combination of energy ranges in which piled-up X-ray photons are included. FIG. 9 illustrates a change in a case of m=3 for reference.

[Case 1]: In a case where m X-ray photons in a low energy range are piled up, and are thus measured as a single X-ray photon in the low energy range, a counted number in the low energy range is reduced by (m−1).

[Case 2]: In a case where m X-ray photons in a low energy range cause pile-up, and are thus measured as a single X-ray photon in a high energy range, a counted number in the low energy range is reduced by m, and a counted number in the high energy range is increased by 1.

[Case 3]: In a case where P (where P is an integer of 1 to (m−1)) X-ray photons in a low energy range of m X-ray photons and (m-P) X-ray photons in a high energy range cause pile-up, and are thus measured as a single X-ray photon in the high energy range, a counted number in the low energy range is reduced by P, and a counted number in the high energy range is reduced by (m-P−1).

[Case 4]: In a case where m X-ray photons in a high energy range cause pile-up, and are thus measured as a single X-ray photon in the high energy range, a counted number in the high energy range is reduced by (m−1).

As mentioned above, if a pile-up occurrence probability in m X-ray photons and a change number according thereto are given, a counting error amount $B_{nm}(i)$ (the letter n added to B indicates an n-th energy range, and the letter m added thereto indicates the number of piled-up X-ray photons) at this time may be expressed as in Equations (4-1) and (4-2) (hereinafter, collectively referred to as Equation (4) in some cases).

[Equation 4]

if $n = 2$ (here, $h(0) = 1$) (4-1)

$$B_{nm}(i) = -\sum_{h(1)=1}^{N}\sum_{h(2)=h(1)}^{N}\ldots\sum_{h(m-2)=h(m-3)}^{N} \alpha_{nNh(1)h(2)\ldots h(m-2)} R_N(i) R_n(i)$$

$$R_{g(1)}(i)R_{g(2)}(i)\ldots R_{g(m-2)}(i) + \sum_{g(1)=1}^{n-1}\sum_{g(2)=g(1)}^{n-1}\ldots$$

$$\sum_{g(m)=g(m-1)}^{n-1} \beta_{g(1)g(2)\ldots g(m)} R_{g(1)}(i) R_{g(2)}(i) \ldots R_{g(m)}(i)$$

if $n = 1$ (4-2)

$$B_{nm}(i) = -\sum_{h(1)=1}^{N}\sum_{h(2)=h(1)}^{N}\ldots\sum_{h(m-1)=h(m-2)}^{N} \alpha_{nh(1)h(2)\ldots h(m-1)} R_n(i) R_{h(1)}(i)$$

$$R_{h(2)}(i)\ldots R_{h(m-1)}(i)$$

In Equation (4), the same symbols as in Equations (2) and (3) have the same meanings. The letters g and h indicating what numbered energy range are differentiated from each other by using numbers in parentheses since a plurality of X-ray photons are included in a corresponding energy range.

The first term of the right side in Equation (4-1) indicates a decrease in the number of X-ray photons in a high energy range in [Case 3], the second term thereof indicates an increase in [Case 2], and the first term of the right side in Equation (4-2) indicates a decrease in the number of X-ray photons in a low energy range in [Case 1], [Case 2], and [Case 3].

In a case where correction is performed in consideration of all of two to M (where M is an integer of 3 or more) pile-ups, $B_n(i)$ may be on the basis of according to Equation (3) with respect to two pile-ups, $B_{nm}(i)$ (where m is 3 to M) may be obtained with respect to three to M pile-ups are obtained according to Equation (4), and a sum thereof may be obtained. The counting error correction process (S7012) is performed by using the counting error amount $B_{nm}(i)$ determined in the above-described way, and this is the same as in a case where the number of piled-up X-ray photons is two.

It is possible to perform highly accurate correction by taking into consideration pile-up of three or more X-ray photons.

Figure 10:
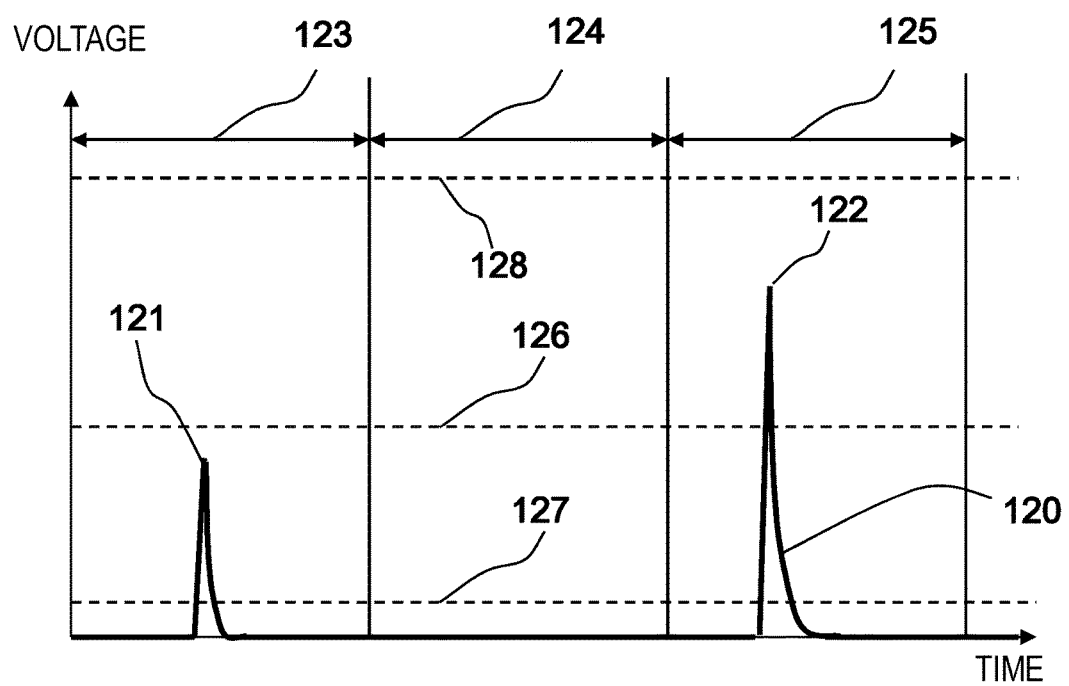
FIG. 10 is a diagram for explaining an energy classifying method which is different from that in FIG. 4, performed by the X-ray detection element in FIG. 3.

Equation (3) or (4) uses a change number due to pile-up derived on the basis of a case where classification of an energy range is performed by using two threshold values (the threshold value 126 and the threshold value 127 in FIG. 5), but the present invention is not limited thereto and is also applicable to a case where three or more threshold values are set. For example, as illustrated in FIG. 10, a threshold value 128 defining the maximum energy may be further provided. Here, in a case of a signal having energy equal to or more than the threshold value 128 due to pile-up, there is no signal which is not piled up, and thus all signals are piled up. In this case, energy more than the threshold value 128 may be considered as a second energy range so as to be added to computation. At this time, counting omission does not occur in this range, and counted amounts are all a counting redundancy amount, and, since there is no signal which is not piled up, Equation (4-1) may be rewritten as Equation (5-1).

[Equation 5]

if $n = 2$ (here, $h(0) = 1$)      (5-1)

$$B_{nm}(i) = -\sum_{g(1)=1}^{n-1} \sum_{g(2)=g(1)}^{n-1} \cdots \sum_{g(m)=g(m-1)}^{n-1} \beta_{g(1)g(2)\ldots g(m)} R_{g(1)}(i) R_{g(2)}(i) \ldots R_{g(m)}(i)$$

if $n = 1$      (5-2)

$$B_{nm}(i) = -\sum_{h(1)=1}^{N-1} \sum_{h(2)=h(1)}^{N-1} \cdots \sum_{h(m-1)=h(m-2)}^{N-1} \alpha_{nh(1)h(2)\ldots h(m-1)} R_n(i) R_{h(1)}(i) R_{h(2)}(i) \ldots R_{h(m-1)}(i)$$

Equation (5-2) is the same as Equation (4-2).

According to the present embodiment, since a counting error caused by pile-up is estimated on the basis of a product of a pile-up occurrence probability and a change number in each energy range when pile-up occurs, it is possible to perform correction specialized for pile-up through relatively simple computation, and thus it is possible to obtain projection data in which the counting error is corrected. As a result, it is possible to prevent a reduction in quantitativeness of a CT value, deterioration in substance classifying performance, the occurrence of an artifact, and the like in a reconstructed image created on the basis of the projection data.

As mentioned above, a function of the calculation unit 105 of the X-ray CT apparatus of the first embodiment, particularly, a correction function has been described with reference to the drawings, but an algorithm for determining or correcting a counting error amount in the above-described counted number correction portion (the counting error amount determination part or the counting error correction part) 1053 is only an example, but does not limit the present embodiment, and may be variously modified. Hereinafter, modification examples will be described.

Modification Example 1 of First Embodiment

In the first embodiment, a counting error amount is estimated on the basis of a product of a pile-up occurrence probability and a change number in each energy range when pile-up occurs, and a counting omission amount and a counting redundancy amount are calculated from a model, but, for example, a characteristic function of a counting error amount in each energy range may be derived from simulation results of simulation using various X-ray doses, ray qualities, and objects, and a counting error amount may be obtained by using the function.

In other words, in Modification Example 1, the counting error amount determination part determines a counting error amount by using a characteristic function indicating a relationship between a counted number in each energy range, and a decrease amount (counting omission amount) and/or an increase amount (counting redundancy amount) due to a single pile-up. Here, the characteristic function may be calculated by using counted numbers in respective energy ranges which are acquired under two or more different conditions related to the occurrence of pile-up.

As an example of the characteristic function, a description will be made of a characteristic function which is divided into a counting omission term and a counting redundancy term.

Here, here, counting omission and counting redundancy even in a single energy range depend on not only the number of X-ray photons in the energy range but also the number of X-ray photons other energy ranges, and thus a characteristic function is required to be set as a function of counted numbers in a plurality of energy ranges. In a case where a characteristic function is derived for each of counting omission and counting redundancy, a counting error amount is represented by a function of a counted number of an energy range in which the counting error amount is determined and counted numbers in other energy ranges. A counted number related to counting redundancy is required to be represented by a function of counted numbers in a plurality of energy ranges lower than an energy range thereof. Therefore, a counting error amount $B_n(i)$ in an n-th (where n is an integer of 1 to N) energy range may be expressed as in Equation (6) by using functions $f1_n$ and $f2_n$.

[Equation 6]

$$B_n(i) = f1_n(R_1(i), R_2(i), \ldots, R_N(i)) + f2_n(R_1(i), R_2(i), \ldots, R_{n-1}(i)) \quad (6)$$

In the equation, the function $f1_n$ is a function for calculating a counting omission amount, and the function $f2_n$ is a function for calculating a counting redundancy amount. Counted numbers in respective energy ranges are indicated by $R_1, \ldots,$ and $R_{n-1}$ in the parentheses, and each of the function $f1_n$ and the function $f2_n$ includes product terms of any two or more combinations (including combinations of the same energy range) of the terms in the parentheses. This is because a pile-up occurrence probability is proportional to a product of counted numbers in energy ranges in which two or more piled-up X-ray photons are included.

As an example, Equation (6) is rewritten as in Equation (7) as a polynomial.

[Equation 7]

$$B_n(i) = -\sum_{g=1}^{n}\sum_{h=g}^{n}\alpha_{gh}R_g(i)R_h(i) + \sum_{g=1}^{n-1}\sum_{h=g}^{n-1}\beta_{gh}R_g(i)R_h(i) \quad (7)$$

Here, $\alpha_{hn}$ and $\beta_{hn}$ are parameters, the first term of the right side in Equation (2) shows an example of $f1_n$, and the second term thereof shows an example of $f2_n$.

In Equation (6), the function $f1_n$ is not required to be a function of all of $R_1, \ldots$, and $R_N$, and, similarly, the function $f2_n$ is not required to be a function of all of $R_1, \ldots$, and $R_{n-1}$. For example, the function $f1_n$ may be a function counted numbers of $R_n$ and one or more of $R_1$ to $R_N$. This is because, as described above, counting omission in the n-th energy range occurs when an X-ray photon in the energy and an X-ray photon in an energy range which is the same as or different from the energy are piled up, and thus an X-ray photon is counted in an energy range which is not the n-th energy range.

The function $f2_n$ may be a function of counted numbers of two or more of $R_1$ to $R_{n-1}$. This is because, as described above, counting redundancy in the n-th energy range occurs when X-ray photons in an energy range lower than the n-th energy range are piled up and are thus counted as an X-ray photon in the n-th energy range. Both of the functions are not necessary, and the counting error amount $B_n(i)$ may be represented by only one function.

As another example of a characteristic function, the characteristic function may be obtained without being divided into counting omission and counting redundancy. In this case, the counting error amount $B_n(i)$ may be expressed as in Equation (8) by using a function $f3_n$.

[Equation 8]

$$B_n(i) = f3_n(R_p(i), R_q(i), \ldots) \quad (8)$$

In the equation, the letters p and q subsequent to R are different integers of 1 to n. Such a characteristic function $f3_n$ may be a function of counted numbers of at least two or more of $R_1, \ldots$, and $R_N$, estimated or derived through simulation or from test results. Also in this case, the function $f3_n$ includes product terms of any two or more combinations (including combinations of the same energy range) of the terms in the parentheses.

The characteristic function determined in the above-described way is saved in the storage unit 109, and, for example, the counting error amount determination part 1056 reads the characteristic function from the storage unit 109, and assigns an actually measured counted number in each energy range thereto so as to obtain a counting error amount.

Modification Example 2 of First Embodiment

In the first embodiment, a description has been made of a case where the counting error amount $B_n(i)$ is calculated by the counting error amount determination part 1056 of the counted number correction portion 1053, and input and output characteristics are corrected by the counting error amount correction part 1057, but this is an example and does not limit the present invention. For example, there may be a configuration in which the counted number correction portion 1053 is not provided with the counting error amount determination part 1056, and the counting error amount correction part 1057 directly corrects the raw data 143 by using the parameters 141.

In this case, input and output characteristics indicating a correspondence relationship between a counted value after the influence of pile-up, that is, the counting error amount $B_n(i)$ is corrected, and an input counted number are stored as the parameters 141 stored in the storage unit 109. The input and output characteristics may be obtained by using the characteristic function (for example, the function in Equation (8)) exemplified in the above Modification Example 1. The input and output characteristics stored as the parameters 141 may be stored as a combination of counted numbers after an input is corrected, and may be stored as a function indicating a relationship between counted numbers after an input is corrected.

Here, needless to say, counted values in a plurality of energy ranges is used as the input.

In this modification example, the counted number correction portion 1053 does not perform the counting error amount determination process (S7011) on the raw data 143, and the counting error amount correction part 1057 directly obtains a corrected counted value from an input counted value with respect to each energy range by using the parameters 141 (S7012).

Modification Example 3 of First Embodiment

In the first embodiment, the influence of pile-up is removed or reduced by subtracting the counting error amount $B_n(i)$ from the raw data 143 received from the signal collecting unit 108 in actual scanning, but there may be a process in which a ratio of change amounts of a signal due to pile-up, or a signal amount or a ratio of change results is calculated as a ratio with respect to a reference output, and is removed from the raw data 143, on the basis of a pile-up occurrence probability. Here, the reference output is, for example, an output in a case where pile-up does not occur.

Second Embodiment

A second embodiment is different from the first embodiment in that a classification number of energy ranges is three or more. A configuration of the calculation unit 105 (FIG. 6) and correction procedures (FIG. 7) are used in common, and thus repeated description of each constituent element will be omitted, and the second embodiment will be described with reference to the drawings.

In the following description, it is assumed that energy ranges detected by the X-ray detectors 104 are first to an N-th (where N is an integer of 3 or more) energy ranges in increasing order of energy. For better understanding of description, first, a description will be made of an example in which the counting error amount $B_n(i)$ is determined in a case where pile-up of two X-ray photons mainly occurs, and counted number correction is performed.

Also in the present embodiment, in the same manner as in the first embodiment, in the counting error amount determination process (S7011), a counting error amount is determined by taking into consideration a pile-up occurrence probability and an increase or decrease amount of a counted number due to the pile-up.

A change in a counted number due to pile-up is required to be divided into a case where X-ray photons in the same energy range are incident and a case where X-ray photons in different energy ranges are incident, and each case is required to be divided into a case where energy of an incident X-ray photon is counted as an energy range which is the same as a higher energy range and a case where energy is counted as an energy range higher than the energy range. FIG. 11(a) illustrates changes occurring when such case classification is performed.

When one of incident X-rays related to pile-up is referred to as an incident X-ray 1, and the other thereof is referred to as an incident X-ray 2, energy ranges thereof are illustrated in FIG. 11(a). A k-th (where k is an integer of 1 to N) energy range and an n-th energy range are respectively abbreviated to "k-th" and "n-th", and the incident X-ray 1 is assumed to be included in an energy range which is the same as or lower than that of the incident X-ray 2. A classified and measured energy range is written in the same manner as a classification result. In the table, each of n, m, and k is an integer within a given range in the parentheses.

As illustrated in FIG. 11(a), four cases are considered.

[Case 1]: An X-ray photon in the k-th energy range and an X-ray photon in the k-th energy range are piled up and are thus classified as a single X-ray photon in the k-th energy range. This case occurs in incident X-ray photons in all energy ranges, and thus k is an integer of 1 to N. In this case, a counted number in the k-th energy range is measured to be reduced by 1.

[Case 2]: An X-ray photon in the k-th energy range and an X-ray photon in the k-th energy range are piled up and are thus classified as a single X-ray photon in the n-th (where n is an integer more than k) energy range. In this case, an energy range of an X-ray photon having lower energy may not be the N-th energy range, and thus k is an integer of 1 to (N−1). On the other hand, an energy range of an X-ray photon having higher energy may be the (k+1)-th to N-th energy ranges, and thus n is an integer of (k+1) to N. In this case, a counted number in the k-th energy range is measured to be reduced by 2, and a counted number in the n-th energy range is measured to be increased by 1.

[Case 3]: An X-ray photon in the k-th energy range and an X-ray photon in the n-th (where n is an integer more than k) energy range are piled up and are thus classified as a single X-ray photon in the n-th energy range. In this case, an energy range of an X-ray photon having lower energy may not be the N-th energy range, and thus k is an integer of 1 to (N−1). On the other hand, an energy range of an X-ray photon having higher energy may be the (k+1)-th to N-th energy ranges, and thus n is an integer of (k+1) to N. In this case, a counted number in the k-th energy range is measured to be reduced by 1.

[Case 4]: An X-ray photon in the k-th energy range and an X-ray photon in the n-th (where n is an integer more than k) energy range are piled up and are thus classified as a single X-ray photon in the m-th (where m is an integer more than n) energy range. In this case, an energy range of an X-ray photon having lower energy may not be the N-th energy range, and thus k is an integer of 1 to (N−1). An energy range of an X-ray photon having higher energy may be the (k+1)-th to N-th energy ranges, and thus n is an integer of (k+1) to N. An energy range in which an X-ray photon is may be the (n+1)-th to N-th energy ranges, and thus m is an integer of (n+1) to N. In this case, a counted number in each of the k-th and n-th energy ranges is measured to be reduced by 1, and a counted number in the m-th energy range is measured to be increased by 1.

When considered in the same manner as in the first embodiment on the basis of the above Cases 1 to 4, counting omission occurs when an X-ray photon in a certain energy range and X-ray photons in the certain energy range or in energy ranges other than the certain energy range cause pile-up, and counting redundancy occurs when X-ray photons in energy ranges lower than the certain energy range cause pile-up. Therefore, it can be seen that a counting omission amount can be estimated by using a counted number in a certain energy range and counted numbers in the certain energy range or in energy ranges other than the certain energy range, and a counting redundancy amount can be estimated by using counted numbers in energy ranges lower than the certain energy range.

In other words, the counting error amount $B_n(i)$ may be expressed as in Equations (9-1) to (9-3) (hereinafter, collectively referred to as Equation (9) in some cases).

[Equation 9]

if $n = N$ (9-1)

$$B_n(i) = -\alpha_{nN} R_N(i) R_n(i) + \sum_{g=1}^{n-1}\sum_{h=g}^{n-1} \beta_{gh} R_g(i) R_h(i)$$

if $n = 2$ to $(N-1)$ (9-2)

$$B_n(i) = -\sum_{h=1}^{N} \alpha_{hn} R_h(i) R_n(i) + \sum_{g=1}^{n-1}\sum_{h=g}^{n-1} \beta_{gh} R_g(i) R_h(i)$$

if $n = 1$ (9-3)

$$B_n(i) = -\sum_{h=1}^{N} \alpha_{hn} R_h(i) R_n(i)$$

In Equation (9), the same symbols as in Equation (3) have the same meanings. Here, in Equation (9), the first term having $\alpha_{hn}$ indicates a counting omission amount, the second term having $\beta_{hn}$ indicates a counting redundancy amount, and n is an integer of 3 or more. Therefore, even in a case where there are three or more energy ranges, accurate projection data can be obtained by determining the parameters $\alpha_{hn}$ and $\beta_{hn}$ through simulation in advance, storing the parameters in the storage unit 109 as the parameters 141 in advance, determining a counting error amount by using Equation (9) in the counting error amount determination (S7011), and performing the counting error amount correction process (S7012) by using the counting error amount.

If "n is 2 to (N−1) (where N is only 3 or more)" is given as a prerequisite of Equation (9-2), Equation (9) becomes a general formula (following equation) for a case where the number of energy ranges is two or more, including Equation (2).

[Equation 10]

if $n = N$ $$B_n(i) = -\alpha_{nN} R_N(i) R_n(i) + \sum_{g=1}^{n-1}\sum_{h=g}^{n-1} \beta_{gh} R_g(i) R_h(i)$$

if $n = 2$ to $(N-1)$ (where $N$ is only 3 or more)

-continued $$B_n(i) = -\sum_{h=1}^{N} \alpha_{hn} R_h(i) R_n(i) + \sum_{g=1}^{n-1} \sum_{h=g}^{n-1} \beta_{gh} R_g(i) R_h(i)$$

if $n = 1$ $$B_n(i) = -\sum_{h=1}^{N} \alpha_{hn} R_h(i) R_n(i)$$

Equation (9) represents a case where two X-ray photons cause pile-up, but, also in the present embodiment, a counting error amount in pile-up of three or more X-ray photons may be estimated.

In this case, for example, the pile-up occurrence probability is calculated by using a counted number of X-ray photons in an energy range. The counting omission is estimated by using a counted number of X-ray photons in an energy range in which a counting error amount is determined and counted numbers of X-ray photons in other energy ranges. The counting redundancy is estimated by using a counted number of X-ray photons in an energy range lower than the energy range in which a counting error amount is determined. The counting error amount $B_n(i)$ may be determined by using the pile-up occurrence probability, and an increase or decrease amount (counting omission or counting redundancy) due to the pile-up.

In a case where m (where m is an integer of 3 or more) X-ray photons cause pile-up, changes occurring in the n-th (where n is 1 to N) energy range are classified and collected for each case as a table in FIG. 11 (b). In other cases, changes in the n-th energy range do not occur. Here, the incident X-ray 1 indicates a single or a plurality of X-ray photons in the n-th energy range, and the incident X-ray 2 indicates a single or a plurality of X-ray photons in other energy ranges. The maximum energy range in the incident X-ray 2 is indicated by the k-th (where k is an integer of 1 to N).

[Case 1]: In a case where Q (where Q is an integer of 2 to m) photons of the incident X-ray 1 among m photons and (m-Q) photons of the incident X-ray 2 in an energy range lower than the n-th energy range (that is, k is 1 to (n−1)) cause pile-up, and are thus measured as a single X-ray photon in the n-th energy range, a counted number in the n-th energy range is reduced by (Q−1). This relationship is also established in a case where Q is 1, but, in this case, a change does not occur.

[Case 2]: In a case where P (where P is an integer of 1 to m) photons of the incident X-ray 1 among m photons and (m-P) photons of the incident X-ray 2 in other energy ranges (that is, k is 1 to (n−1) or (n+1) to N) cause pile-up, and are thus measured as a single X-ray photon in the L-th (where L is an integer of above n to N) energy range higher than the n-th energy range, a counted number in the n-th energy range is reduced by P.

This may occur in a case where n is equal to or less than (N−1).

[Case 3]: In a case where m X-ray photons (that is, m photons of the incident X-ray 2 at k of 1 to (n−1)) in energy ranges lower than in the n-th energy range cause pile-up, and are thus measured as a single X-ray photon in the n-th energy range, a counted number in the n-th energy range is increased by 1. This may occur in a case where n is 2 or more.

The counting error amount $B_{nm}(i)$ in this case may be expressed as in Equations (11-1) to (11-3) (hereinafter, collectively referred to as Equation (11) in some cases).

[Equation 11]

if $n = N$ (here, $h(0) = 1$)  (11-1)

$$B_{nm}(i) = -\sum_{h(1)=1}^{N} \sum_{h(2)=h(1)}^{N} \cdots \sum_{h(m-2)=h(m-3)}^{N} \alpha_{nNh(1)h(2)\ldots h(m-2)} R_N(i) R_n(i)$$

$$R_{g(1)}(i) R_{g(2)}(i) \ldots R_{g(m-2)}(i) + \sum_{g(1)=1}^{n-1} \sum_{g(2)=g(1)}^{n-1} \cdots$$

$$\sum_{gm=g(m-1)}^{n-1} \beta_{g(1)g(2)\ldots g(m)} R_{g(1)}(i) R_{g(2)}(i) \ldots R_{g(m)}(i)$$

if $n$ is 2 to $N$  (11-2)

$$B_{nm}(i) = -\sum_{h(1)=1}^{N} \sum_{h(2)=h(1)}^{N} \cdots \sum_{h(m-1)=h(m-2)}^{N} \alpha_{nh(1)h(2)\ldots h(m-1)} R_n(i) R_{h(1)}(i)$$

$$R_{h(2)}(i) \ldots R_{h(m-1)}(i) + \sum_{g(1)=1}^{n-1} \sum_{g(2)=g(1)}^{n-1} \cdots$$

$$\sum_{gm=g(m-1)}^{n-1} \beta_{g(1)g(2)\ldots g(m)} R_{g(1)}(i) R_{g(2)}(i) \ldots R_{g(m)}(i)$$

if $n = 1$  (11-3)

$$B_{nm}(i) = -\sum_{h(1)=1}^{N} \sum_{h(2)=h(1)}^{n} \cdots \sum_{h(m-1)=h(m-2)}^{N} \alpha_{nh(1)h(2)\ldots h(m-1)} R_n(i) R_{h(1)}(i)$$

$$R_{h(2)}(i) \ldots R_{h(m-1)}(i)$$

Here, Equation (11-1) corresponds to a case of n=N, the first term of the right side represents a decrease amount in [Case 1], and the second term of the right side represents an increase amount in [Case 3]. Here, Equation (11-2) corresponds to a case where n is 2 to (N−1), the first term of the right side represents a decrease amount in [Case 1] and [Case 2], and the second term of the right side represents an increase amount in [Case 3]. Here, Equation (11-3) corresponds to a case of n=1, the right side represents a decrease amount in [Case 1] and [Case 2]. Here, there is the first term of the right side in Equation (11-2) or the term of the right side in Equation (11-3) showing combinations other than [Case 1] and [Case 2], but the parameter a is zero and is not substantially used.

In a case where correction is performed in consideration of all of two to M (where M is an integer of 2 or more) pile-ups, $B_n(i)$ may be on the basis of according to Equation (8) with respect to two pile-ups, $B_{nm}(i)$ (where m is 3 to M) may be obtained with respect to three to M pile-ups are obtained according to Equation (9), and a sum thereof may be obtained. The counting error correction process (S7012) is performed by using the counting error amount $B_{nm}(i)$ determined in the above-described way, and this is the same as in a case where the number of piled-up X-ray photons is two.

It is possible to perform highly accurate correction by taking into consideration pile-up of three or more X-ray photons.

As mentioned above, the function of the counted number correction portion of the X-ray CT apparatus of the second embodiment has been focused, but the present embodiment may be modified in the same manner as the modification example of the first embodiment. Also in the present embodiment, there may be a configuration in which only one of counting omission and counting redundancy in a counting error is employed.

According to the present embodiment, also in the X-ray CT apparatus including the X-ray detectors 104 which can classify energy into three or more energy ranges, in the same manner as in the first embodiment, it is possible to correct a counting error due to pile-up with high accuracy and thus to obtain projection data in which the counting error is corrected. It is possible to prevent a reduction in quantitativeness of a CT value, deterioration in substance classifying performance, the occurrence of an artifact, and the like in a reconstructed image created on the basis of the projection data.

Third Embodiment

In the first embodiment and the second embodiment, a description has been made of a case where parameters used for equations for determining a counting error amount are obtained through simulation, but the parameters may be calculated on the basis of values actually measured by using an X-ray CT apparatus.

An X-ray CT apparatus of the present embodiment is characterized in terms of having a function of experimentally determining parameters for determining a counting error amount due to pile-up. In other words, the X-ray CT apparatus of the present embodiment further includes a parameter calculation part which calculates parameters, and the parameter calculation part calculates parameters by using counted numbers in respective energy ranges which are obtained through measurement under two or more different conditions related to the occurrence of pile-up.

The two or more conditions related to the occurrence of pile-up include, for example, a condition regarding a dose of X-rays incident to the X-ray detector. One of the two or more conditions related to the occurrence of pile-up is a condition in which a dose of X-rays incident to the X-ray detector does not cause pile-up.

FIG. 12 illustrates the entire configuration of the X-ray CT apparatus of the present embodiment, and FIG. 13 illustrates a configuration of a calculation unit. In FIGS. 12 and 13, the same constituent elements as the constituent elements illustrated in FIGS. 1 and 6 which are referred to in description of the first and second embodiments are given the same reference numerals, repeated description thereof will be omitted, and description will be made focusing on differences.

As illustrated in FIG. 12, the X-ray CT apparatus of the present embodiment includes a dose changing unit 114 which changes an X-ray dose, and a ray quality changing unit 115 which changes a ray quality. The dose changing unit 114 and the ray quality changing unit 115 may be a part of the control unit 107, and may be an adjustment mechanism which is independent from the control unit 107.

Generally, a dose of X-rays is changed due to a tube current, and ray quality is changed due to a tube voltage or a filter. A driving unit of an X-ray tube forming the X-ray source 100 has a function of changing a tube current and a tube voltage. The X-ray source 100 includes X-ray filters 113 made of various metals for obtaining effective ray quality according to energy, and a switching mechanism which automatically or manually switch among a plurality of kinds of X-ray filters. The dose changing unit 114 and the ray quality changing unit 115 of the present embodiment are operated under the control of the control unit 107, and, a dose or ray quality is changed by controlling, for example, a driving unit (a tube current or a tube voltage) of the X-ray source 100 or a switching mechanism unit of the X-ray filters 113.

In the calculation unit 105 of the X-ray CT apparatus of the present embodiment, as illustrated in FIG. 13, a parameter calculation part 1058 is added to the counted number correction portion 1053. The parameter calculation part 1058 calculates parameters used for the signal collecting unit 108 to calculate a counting error amount by using raw data which is actually measured under a plurality of conditions in which one or more of a dose, ray quality, and a filter are changed.

Figure 14:
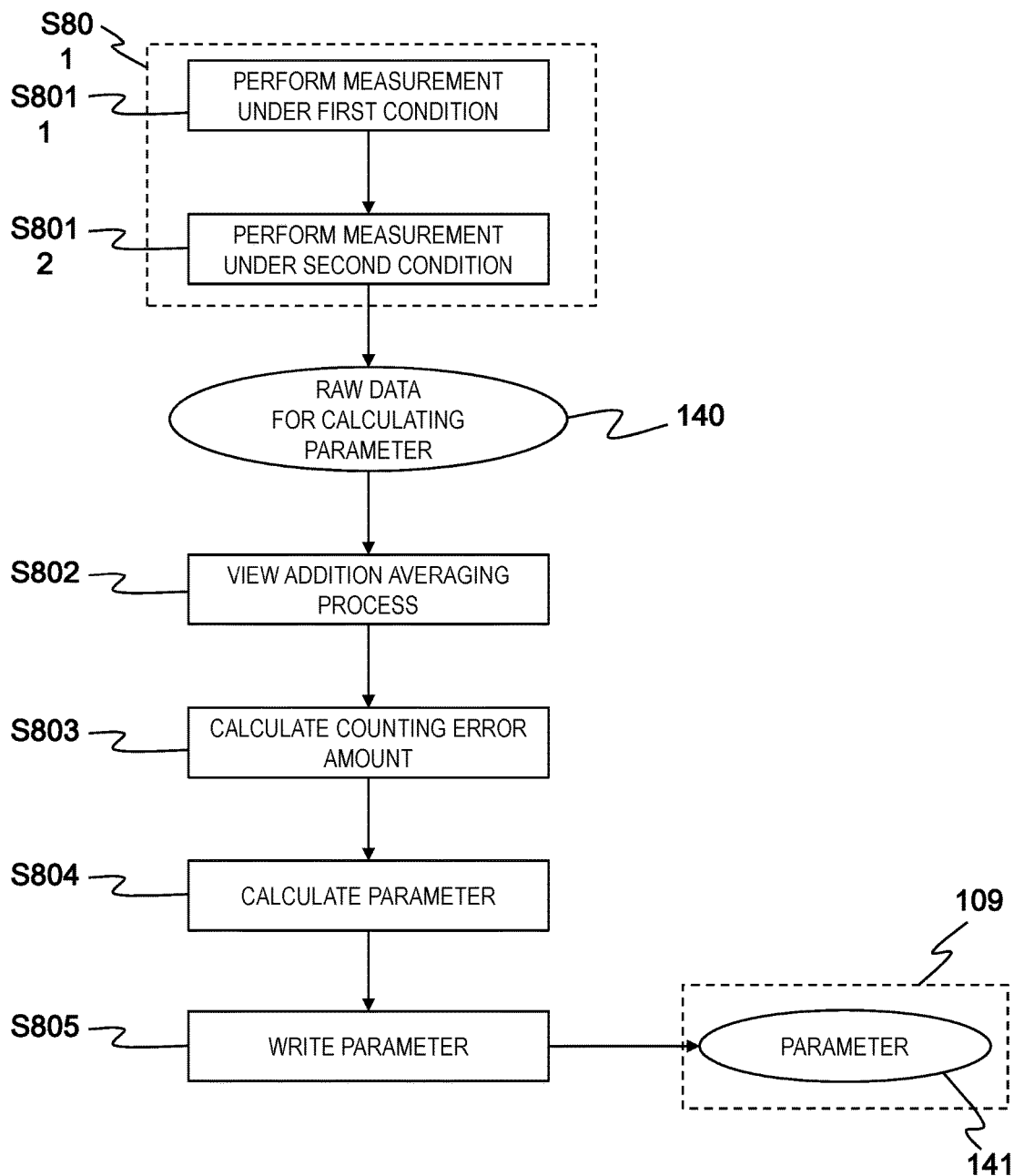
FIG. 14 is a diagram illustrating a flow of determining a parameter in a parameter calculation part of the third embodiment.

Hereinafter, in the present embodiment, with reference to FIG. 14, a description will be made of procedures (mainly, operations of the control unit 107 and the calculation unit 105) of calculating the parameters $\alpha_{hn}$ and $\beta_{hn}$ in a computation formula (for example, Equation (3)) used by the counting error amount determination part 1056 of the first embodiment or a computation formula (for example, Equation (9)) used by the counting error amount determination part 1056 of the second embodiment.

First, the control unit 107 controls the X-ray source 100 and the X-ray detectors 104 so as to perform scanning under a plurality of different conditions, and obtains raw data for calculating parameters (S801). For example, raw data is acquired by the X-ray detectors 104 while applying X-rays from the X-ray source 100 with a single ray quality and a predetermined X-ray dose (first condition). At this time, signals corresponding to a plurality of views are acquired (S8011). Next, raw data is acquired under a second condition in which an X-ray dose is changed by the dose changing unit 114 (S8012). Raw data may be acquired under third, ..., and L-th (where L is an integer of 3 or more) conditions in which X-ray doses are changed. Next, the ray quality changing unit 115 changes a ray quality, and raw data is acquired at a differing ray quality under the first condition and the second condition (or the second to L-th conditions).

The first condition is a condition in which it is considered that an X-ray dose is sufficiently low with respect to a single ray quality, and pile-up does not occur, and raw data acquired under the first condition is used as reference data. The second and subsequent conditions are conditions in which an X-ray dose is high, and pile-up occurs, and raw data acquired under these conditions is referred to as pile-up data. When a set of data formed of the reference data and pile-up data is acquired, an X-ray dose is simultaneously measured by using an X-ray dosimeter (not illustrated). The set of data is used as parameter calculation data 140.

Next, the calculation unit 105 (parameter calculation part 1058) calculates the parameters $\alpha_{hn}$ and $\beta_{hn}$ by using the acquired raw data for calculating parameter 140. In this computation, first, a view addition averaging process (S802) of obtaining an addition average in a view direction is performed on the raw data for calculating parameter 140. Consequently, the data is compressed, and thus an SNR can be increased.

Next, a counting error amount calculation process (S803) is performed. In this process, first, the reference data is multiplied by a dose ratio (the dose ratio=a dose when the pile-up data is acquired/a dose when the reference data is acquired), and thus an output corresponding to an X-ray dose at which the pile-up data is acquired is calculated. A difference between the output and an output of the pile-up data is obtained. The output calculated from the reference data has no influence of pile-up, and thus a difference between this data and the pile-up data is the counting error amount $B_n(i)$. The counting error amount calculation process (S803) is performed in all energy ranges for each X-ray detection element 400.

Next, in a parameter determination process (S804), the parameters $\alpha_{hn}$ and $\beta_{hn}$ are determined. Specifically, the counting error amount $B_n(i)$ obtained in the process (S803) and a value of the pile-up data are assigned to Equation (3) or Equation (9), simultaneous equations are solved, and thus the parameters $\alpha_{hn}$ and $\beta_{hn}$ can be determined. In a case of Equation (3) in which energy is classified into two kinds of energy ranges, four parameters such as $\alpha_{11}$, $\alpha_{12}$, $\alpha_{22}$, and $\beta_{11}$ are required to be determined as the parameters $\alpha_{hn}$ and $\beta_{hn}$. Therefore, four or more pairs of parameter calculation data 140 are necessary, and data is required to be acquired with four or more kinds of ray qualities. In a case where there are four or more pairs, simultaneous equations for the four pairs may be provided for calculating the parameters, and the parameters may be determined by using a least square method.

Also in a case where energy is classified into N (where N is 3 or more) energy ranges, that is, in a case of Equation (9), the counting error amount $B_n(i)$ obtained in the process (S803) and a value of the pile-up data are assigned to Equation (9), simultaneous equations are solved, and thus the parameters $\alpha_{hn}$ and $\beta_{hn}$ can be determined. As can be seen from Equation (9), since there are N $\alpha_{hn}$ if an energy range is the first to (N−1)-th energy ranges, and there is single $\alpha_{hn}$ if an energy range is the N-th energy range, a total of $(N^2-N+1)$ $\alpha_{hn}$ are present. When an energy range is the n-th energy range among the second to N-th energy ranges, $(n-1)^2$ $\beta_{hn}$ are present. Therefore, a total of the parameters $\alpha_{hn}$ and $\beta_{hn}$ to be determined is $\{(2N^3+3N^2-5N+6)/6\}$, and the parameter calculation data 140 of the same number as or a larger number than this is necessary.

Finally, the parameters $\alpha_{hn}$ and $\beta_{hn}$ determined in the above-described way are written to the storage unit 109 as the parameters 141 in the process (S805). Thereafter, a counting error amount is determined (FIG. 7: S7011), the counting error amount is corrected (FIG. 7: S7012), by using the parameters, so that projection data is obtained, and an image is reconstructed by using the projection data, in the same manner as in the first embodiment and the second embodiment.

A description has been made of a case where, in Modification Example 1 of the first embodiment, a counting error amount is determined by using Equations (6) to (8) characteristic functions instead of Equation (3) using the parameters $\alpha_{hn}$ and $\beta_{hn}$ in the counting error amount determination (S7011), but, when the equations are used, the parameter calculation part 1058 calculates, for example, coefficients of the characteristic functions as the parameters 141.

According to the present embodiment, parameters are determined on the basis of actually measured data, and thus the reliability of counting error amount calculation can be improved. If the parameters are determined once, values saved in the storage unit 109 can be used thereafter, and thus there is no influence to an operation of the X-ray CT apparatus.

The same modifications as in the first and second embodiments may occur in the present embodiment, and, further, the following modifications may occur.

Modification Example 1 of Third Embodiment

For example, a scanning condition such as a tube current may be used instead of using a dose measured by a dosimeter as a condition (a condition to be changed) when parameters are experimentally obtained.

In the third embodiment, the ray quality changing unit 115 changes a ray quality by changing a tube current or an X-ray filter, and acquires data through scanning, but a ray quality may be changed by providing an attenuator as the object 300. A ray quality may be changed by combining one or two of a tube current, the X-ray filters 113, and the object 300.

Modification Example 2 of Third Embodiment

There may be a case where all parameters are not determined experimentally, and some of the parameters are determined through simulation in computation.

Fourth Embodiment

An X-ray CT apparatus of the present embodiment is different from that of the first embodiment in that the counting error amount $B_n(i)$ is determined by using a sum of counted numbers of X-ray photons in a plurality of energy ranges.

In the present embodiment, a counting error amount determination part determines a pile-up occurrence probability according to a total of counted numbers of X-ray photons in all energy ranges. A counting error amount is determined on the basis of a product of the pile-up occurrence probability determined according to the sum of counted numbers of X-ray photons in all energy ranges and a preset parameter.

A configuration of the calculation unit 105 and a flow of a process performed by the calculation unit 105 of the present embodiment are the same as those in FIGS. 6 and 7, and, hereinafter, a process in the calculation unit 105 of the present embodiment will be described with reference to the drawings as appropriate.

Also in the present embodiment, the counted number correction portion 1053 calculates a pile-up occurrence probability by using counted numbers in a plurality of energy ranges and the parameters 141 on the basis of the raw data 143, and determines a counting error amount (S7011), and corrects a counting error amount in the raw data 143 (S7012). However, in the present embodiment, the counting error amount determination part 1056 determines a pile-up occurrence probability not by using a product of counted numbers in energy ranges related to pile-up but by using a sum of counted numbers. Thus, parameters 141 which are different from those in the first embodiment are obtained in advance and are stored in the storage unit 109. The following Equation (12) is an example of an equation for determining the counting error amount $B_n(i)$ in the counting error amount determination part 1056.

[Equation 12]

$$B_n(i) = \Delta_n(i) \cdot \left( \sum_{j=1}^{N} R_j(i) \right)^2 \qquad (12)$$

In the equation, $R_j(i)$ indicates a counted number in a j-th energy range in an i-th (where i is an integer of 1 or more) X-ray detection element. $\Delta_n(i)$ is a counting error amount calculation parameter.

As mentioned above, in Equation (12), the counting error amount is calculated by multiplying the square of a sum of counted numbers in all energy ranges obtained through actual scanning by the counting error amount calculation parameter $\Delta_n(i)$. The counting error amount $B_n(i)$ is determined for each X-ray detection element by using Equation (12) (S7011).

In the present embodiment, a counting error amount is determined as an amount which depends on a dose instead of taking into consideration individual energy ranges of piled-up X-ray photons as in the first embodiment or the second embodiment. Here, a sum of counted numbers in all energy ranges is used as the dose. In this case, a pile-up occurrence probability in each energy range depends on a whole number of X-ray photons.

For example, in a case of the number of incident X-ray photons to the extent to which pile-up of three or more X-ray photons is negligible, a probability of two X-ray photons being piled up is substantially proportional to the square of the whole number of X-ray photons. On the other hand, a change amount due to a single pile-up is an average value of various counting omissions and counting redundancies analyzed in the second embodiment (Table 11), and is substantially constant unless an energy distribution greatly changes. Therefore, a counting error amount can be approximated to a product of the square of the whole number of X-ray photons and a change amount due to a single pile-up. The whole number of X-ray photons is substantially proportional to the square of a sum of counted numbers in all energy ranges, and thus a counting error amount may be estimated by using the square of a sum of counted numbers in all energy ranges.

Equation (12) does not include a term of a change amount due to a single pile-up, but, if a value including a change amount due to a single pile-up is obtained as the parameter $\Delta_n(i)$, the counting error amount $B_n(i)$ can be calculated according to Equation (12).

For example, in simulation according to a Monte Carlo method, counted numbers in each energy range are obtained in a case where there is the influence of pile-up and a case where there is no influence of the pile-up when the number of input X-ray photons are changed and X-rays are incident to the X-ray detectors 104, and the parameter $\Delta_n(i)$ is obtained by assigning a difference therebetween as the counting error amount $B_n(i)$ to Equation (12).

Here, the simulation for obtaining a counted number in a case where there is the influence of pile-up may employ the same method as the method described with reference to FIG. 5 in the first embodiment, for example. In other words, the same sampling period of time as in actual measurement is provided, and a temporal wave height change in a case where a single X-ray photon is incident is simulated, and a temporal wave height change is simulated in which overlapping of a plurality of incident X-ray photons is taken into consideration. In simulation in a case where there is no influence of pile-up, a sampling period of time is not provided, and a counted number is calculated on the basis of energy of each X-ray photon. The counting error amount calculation parameter $\Delta_n(i)$ due to pile-up can be determined on the basis of a difference between respective counted numbers by performing such simulation.

In the above-described way, a counting error amount is determined (S7011), a counting error amount in the raw data 143 is corrected (S7012), then, LOG conversion (S702) and air correction (S703) are performed so that corrected projection data 144 is obtained, reconstruction (S704) is performed by using the corrected projection data 144, and a reconstructed image is displayed as necessary (S705) in the same manner as in the first and second embodiments.

In the above description, a description has been made of a case where, in the counted number correction portion 1053, the counting error amount determination part 1056 calculates the counting error amount $B_n(i)$, and the counting error amount correction part 1057 corrects input and output characteristics, but, as described in Modification Example 2 of the first embodiment, there may be a configuration in which the counting error amount correction portion 1053 is not provided with the counting error amount determination part 1056, and the counting error amount correction part 1057 directly corrects raw data by using the parameters 141. In this case, a sum of counted numbers in a plurality of energy ranges is used as inputs of the parameters 141 stored in the storage unit 109, and thus a data amount is smaller than in a case (first embodiment) where a counted number in each energy range is used.

According to the present embodiment, in the same manner as in the above-described embodiments, a counting error due to pile-up can be corrected with high accuracy, and thus projection data in which the counting error is corrected can be obtained. It is possible to prevent a reduction in quantitativeness of a CT value, deterioration in substance classifying performance, the occurrence of an artifact, and the like in a reconstructed image created on the basis of the projection data.

Modification Example 1 of Fourth Embodiment

In the present embodiment, a counting error amount is calculated by using the fact that a pile-up occurrence probability depends on a dose, that is, a whole counted number, and a formula employed by the counting error amount determination part 1056 may be variously modified on the basis of the above Equation (12) as long as the formula is in line with the purpose thereof.

In other words, in Equation (12), the counting error amount $B_n(i)$ is described by only on the term of the square of the whole number of X-ray photons, but there may be cases of various characteristic functions having terms other than the square term.

For example, a probability of two X-ray photons among M X-ray photons being piled up is proportional to $_MC_2$ ($=0.5M \times (M-1)$), and thus has not only a square term but also a linear term. There may be a case where terms other than a square term may be included due to a change in an energy distribution. For example, a polynomial such as the following Equation (13) may be used.

[Equation 13]

$$B_n(i) = a\Delta_n(i) \cdot \left(\sum_{j=1}^{N} R_j(i)\right)^3 + b\Delta_n(i) \cdot \left(\sum_{j=1}^{N} R_j(i)\right)^2 + c\Delta_n(i) \cdot \left(\sum_{j=1}^{N} R_j(i)\right) \quad (13)$$

Here, needless to say, there may be a case where coefficients (parameters) of respective terms are different from each other.

The counting error amount calculation parameter $\Delta_n(i)$ in the n-th energy range or $a \cdot \Delta_n(i)$ in Equation (13) is used as the parameters 141, but a characteristic function having a sum of counted numbers as a variable may be used. The characteristic function may be expressed as in Equation (14) by using a function $h_n$.

[Equation 14]

$$B_n(i) = h_n\left(\sum_{j=1}^{N} R_j(i)\right) \quad (14)$$

The function $h_n$ has at least an M-th order term to a second order term, for example, in a case where pile-up of M (where M is an integer of 2 or more) X-ray photons is taken into consideration.

The counting error amount $B_n(i)$ may be zero, for example, if a sum of counted numbers is less than a threshold value, and may be characteristic functions which are different from each other in ranges partitioned by the threshold value if the sum thereof is equal to or more than the threshold value, for example, by using the values of Equations (12) to (14). There may be a case where a characteristic function continuously changes due to a sum of counted numbers.

Modification Example 2 of Fourth Embodiment

In the fourth embodiment, a sum of counted numbers in all energy ranges is used as a dose for determining a pile-up occurrence probability, but a dose is not limited to a sum of counted numbers, and amounts for estimating a dose may be used.

For example, a dose may be calculated on the basis of a sum of counted numbers in energy ranges of a number which causes the dose to be estimated, for example, on the basis of a sum of counted numbers in a single energy range or various combinations of a plurality of energy ranges. Here, the sum may be calculated by using a constant weight or different weights, and, needless to say, it is preferable to use counted numbers in many energy ranges in order to estimate a dose with high accuracy.

Alternatively, an assumed object may be used, and a value calculated through simulation may be used as a dose. A result (dose) measured by a separate dosimeter or an X-ray detector which can measure a dose may be used. As a structure of the X-ray detector which can measure a dose, there may be a structure in which, for example, some X-ray detection elements of the X-ray detector have a circuit configuration which are not of a pulse counting type and do not cause pile-up, for example, the X-ray detection elements have a current measurement type reading circuit, and can estimate a dose on the basis of an output value therefrom, or a structure in which a single X-ray detection element has both of a pulse counting type reading circuit and a current measurement type reading circuit, and estimates a dose on the basis of an output value from the current measurement type reading circuit.

Fifth Embodiment

Also in the present embodiment, in the same manner as in the fourth embodiment, the counting error amount $B_n(i)$ is determined by using a dose (a sum of counted numbers of X-ray photons in a plurality of energy ranges). However, whereas, in the fourth embodiment, the parameters 141 used for calculation of a counting error amount are obtained through simulation, in the present embodiment, the parameters 141 are calculated by using experimentally obtained data.

In other words, an X-ray CT apparatus of the present embodiment further includes a parameter calculation part which calculates parameters. The parameter calculation part calculates parameters by using counted numbers in respective energy ranges which are acquired through measurement under two or more different conditions related to the occurrence of pile-up. The two or more conditions related to the occurrence of pile-up include, for example, a condition regarding a dose of X-rays incident to the X-ray detector, and one of the two or more conditions related to the occurrence of pile-up is a condition in which a dose of X-rays incident to the X-ray detector does not cause pile-up.

Hereinafter, the present embodiment will be described focusing on differences from the fourth embodiment.

Figure 15:
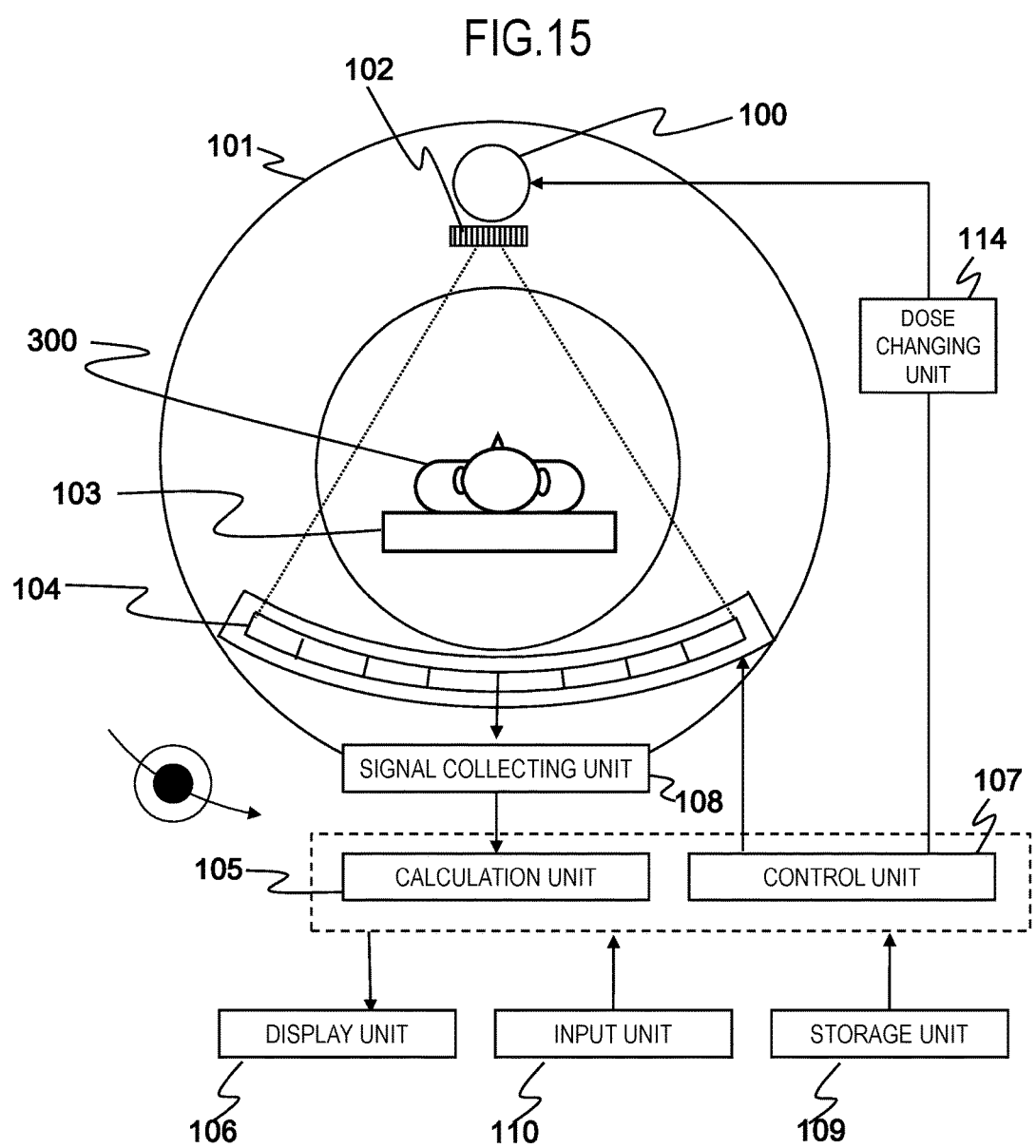
FIG. 15 is a schematic diagram illustrating a configuration of an X-ray CT apparatus of a fifth embodiment.

FIG. 15 illustrates the entire schematic configuration of the X-ray CT apparatus for implementing the present embodiment. In FIG. 15, the same constituent elements as the constituent elements illustrated in FIG. 1 which is referred to in description of the first embodiment are given the same reference numerals, repeated description thereof will be omitted, and description will be made focusing on differences.

The X-ray CT apparatus includes a dose changing unit 114 which changes an X-ray dose. A driving unit (not illustrated) of an X-ray tube forming the X-ray source 100 has a function of changing a tube current. The dose changing unit 114 may be a part of the control unit 107, and is operated under the control of the control unit 107. The driving unit of the X-ray source 100 controls, for example, a tube voltage so as to change a dose.

The calculation unit 105 has the same configuration as the configuration illustrated in FIG. 13 referred to in description of the third embodiment, and thus the parameter calculation part 1058 is added to the counted number correction portion 1053. The parameter calculation part 1058 calculates parameters used to calculate a counting error amount by using raw data which is actually measured under a plurality of conditions in which a dose is changed in the signal collecting unit 108.

Hereinafter, in the present embodiment, with reference to FIG. 16, a description will be made of procedures (mainly, operations of the parameter calculation part 1058) of calculating the parameters 141 in a computation formula (for example, Equation (12)) used by the counting error amount determination part 1056 of the fourth embodiment.

First, the control unit 107 controls the dose changing unit 114, the X-ray source 100, and the X-ray detectors 104 according to scanning conditions 148 which are set via the input unit 105 (S901), and obtains raw data for calculating parameters (S901). For example, raw data is acquired with a predetermined X-ray dose (first condition) (S9011). Next, raw data is acquired under a second condition in which an X-ray dose is changed (S9012). The first condition is a condition in which an X-ray dose is low, and the occurrence of pile-up is substantially negligible. The second condition is a condition in which an X-ray dose is high, and pile-up occurs. The raw data for calculating parameter 140 which is a set of raw data acquired under the first condition and the second condition is obtained in the above-described way.

Next, the parameter calculation part 1058 performs a view addition averaging process on the raw data 140 (S902). Consequently, the data is compressed, and thus an SNR can be increased. Simultaneously, the parameter calculation part 1058 estimates an X-ray dose ratio on the basis of the designated scanning conditions 148 (S903).

Here, as the scanning conditions 148, an X-ray dose ratio is estimated, which is a ratio of a dose in the second condition to a does in the first condition by using, for example, a tube current.

Next, the parameter calculation part 1058 calculates a counting error amount by using the raw data (hereinafter, referred to as counting error amount calculation data) having undergone the addition averaging and the X-ray dose ratio estimated in S903 (S904).

In the counting error amount calculation (S904), a difference between an ideal counted number of X-ray photons not causing pile-up and an actual counted number of X-ray photons causing pile-up in each energy range under the second condition is calculated, so as to be assigned to the counting error amount $B_n(i)$ in Equation (12), and thus the counting error amount calculation parameter $\Delta_n(i)$ is calculated.

Here, the ideal counted number of X-ray photons not causing pile-up under the second condition is calculated by multiplying the counting error amount calculation data obtained under the first condition by the X-ray dose ratio (S905). Therefore, the parameter calculation part 1058 determines the counting error amount calculation parameter $\Delta_n(i)$ by performing computation according to, for example, Equation (15).

[Equation 15]

$$\Delta_n(i) = \frac{H \cdot R[1]_n(i) - R[2]_n(i)}{\left(\sum_{j=1}^{N} R[2]_j(i)\right)^2} \quad (15)$$

In Equation (15), $R[r]_i(i)$ indicates a counted number in a j-th energy range under an r-th (where r is an integer of 1 or 2) condition, and H indicates an X-ray dose ratio. The numerator of the right side in Equation (15) indicates "a difference between an ideal counted number of X-ray photons not causing pile-up and an actual counted number of X-ray photons causing pile-up", and will be hereinafter referred to as characteristic data.

The parameter calculated in the above-described way is written to the storage unit 109 (S906). The parameters 141 saved in the storage unit 109 are substantially used for the counted correction portion 1056 to determine and/or correct a counting error amount with respect to raw data obtained after the present scanning (FIG. 7: S7011 and S7012). Other processes are the same as in the fourth embodiment or modification examples thereof, and thus description thereof will be omitted.

In the above description, the description has been made of a case where the parameters 141 are determined by using characteristic data obtained through scanning under two scanning conditions, but this is only an example, and characteristic data obtained through scanning under three or more scanning conditions may be used. In this case, the added scanning condition is preferably a dose which causes pile-up, and is different from doses in other scanning conditions. Particularly, it is possible to increase the accuracy of determining a characteristic function by using characteristic data in many scanning conditions.

In the above description, the description has been made of a case of the counting error amount calculation parameter $\Delta_n(i)$ used for Equation (12) as the parameters 141, but, as exemplified in the modification example of the fourth embodiment, needless to say, if a computation formula used by the counting error amount determination part 1056 differs, a counting error amount calculation parameter to be obtained naturally differs according thereto. In other words, for example, in a case of a polynomial such as Equation (13), coefficients thereof are obtained as parameters. There may be a case of a characteristic function. In either case, parameters can be obtained by assigning characteristic data obtained through actual measurement to the equation. In this case, a plurality of pieces of characteristic data in which dose conditions are different from each other may be obtained according to the number of parameters.

The characteristic data may be saved in the storage unit 109 as the parameters 141, the characteristic data may be read from the storage unit 109 whenever actual scanning is performed, and the counted number correction portion 1056 may calculates the counting error amount $B_n(i)$.

Modification Example of Fifth Embodiment

In the fifth embodiment, when actually measured data is obtained by changing conditions, the dose changing unit 114 realizes the first condition and the second condition by changing an X-ray dose, but a technique of changing conditions is not limited thereto. For example, the same dose as in the second condition may be used, and the first condition may be acquired by providing an attenuator in an object without using the dose changing unit 114. In this case, as the attenuator, a material similar to a human body, such as water, is preferably used. In a case where the attenuator is used as mentioned above, a ray quality also changes along with a dose, but the ray quality also similarly changes in a case where an actual object is scanned, and thus it is possible to determine the parameters 141 on the basis of more realistic characteristic data. Therefore, it is possible to calculate the counting error amount $B_n(i)$ with higher accuracy and thus to improve correction accuracy in actual scanning.

Regarding changing of conditions, not only a dose but also both a dose and a ray quality may be changed. This modification example may be implemented by the X-ray CT apparatus including the ray quality changing unit 113 in addition to the dose changing unit 114, as illustrated in FIG. 12 referred to in description of the third embodiment.

Figure 16:
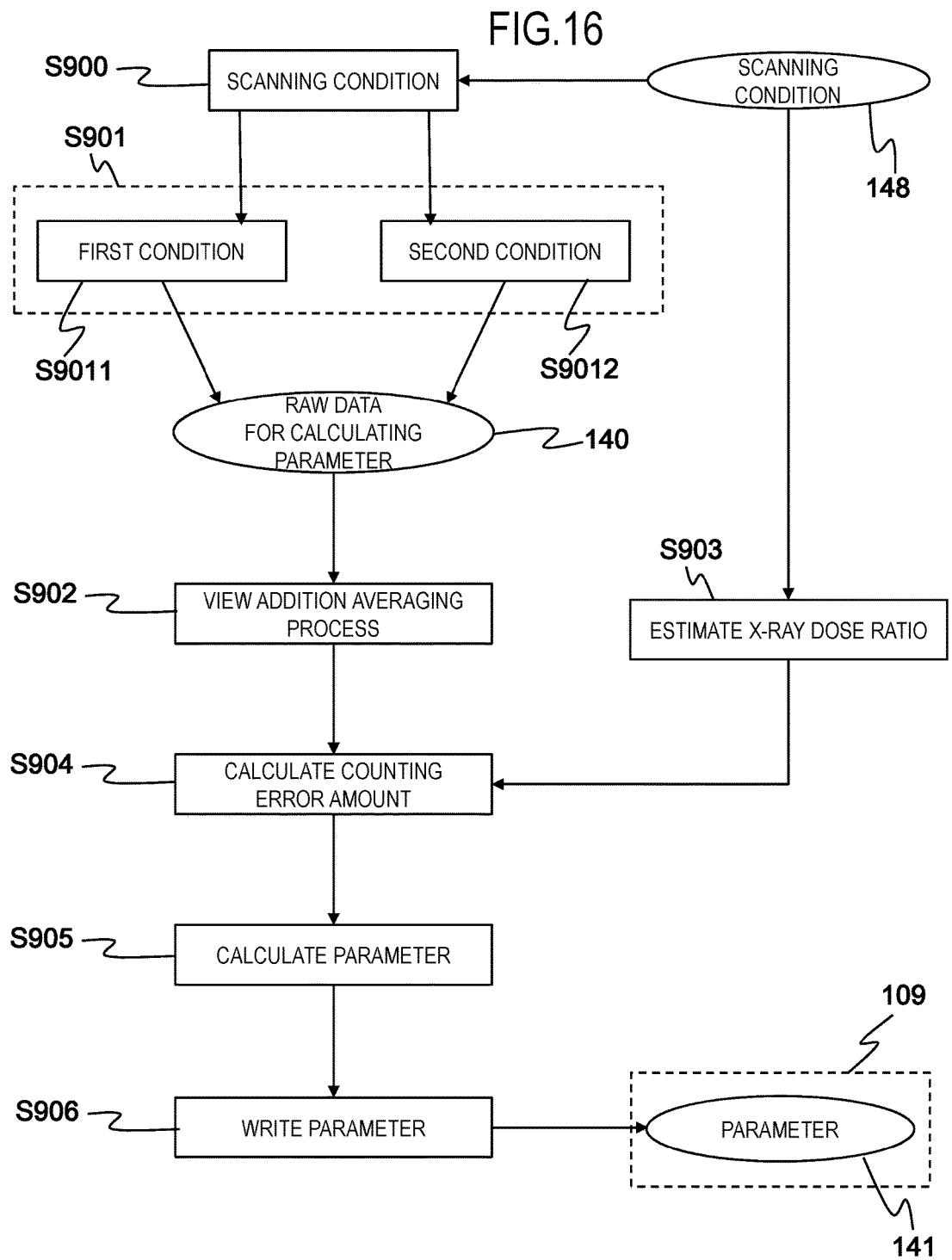
FIG. 16 is a diagram illustrating a flow of determining a parameter in the X-ray CT apparatus of the fifth embodiment.

A description has been made of a case where, in the process (S903) in FIG. 16, an X-ray dose is determined by using a tube current when an X-ray dose ratio is estimated, but various measurement amounts which depend on an X-ray dose in the first and second conditions may be used in addition to a tube current.

For example, an X-ray dose measured by using a dosimeter may be used. Measurements under the first condition and the second condition may not be performed separately, but one measurement may be performed under two conditions.

For example, there may be a configuration in which an attenuator is provided on a part of an X-ray incidence surface of the X-ray detectors 104, X-rays are attenuated so that an X-ray dose is reduced to the extent to which pile-up is negligible even under the second condition (a pile-up occurrence condition), measurement is performed under the second condition, a counted number in the attenuator is used as a counted number obtained under the first condition, a counted number in a portion where the attenuator is not provided is used as a counted number obtained under the second condition, and an X-ray dose may be determined.

Alternatively, there may be a configuration in which incidence areas of some of the X-ray detection elements of the X-ray detectors 104 are reduced so that the number of incident X-ray photons is reduced to the extent to which pile-up does not occur even under the second condition (pile-up occurrence condition), measurement is performed under the second condition, a counted number in the X-ray detection elements whose incidence areas are reduced is used as a counted number under the first condition, and a counted number in other X-ray detection elements is used as a counted number under the second condition. An X-ray detector not causing pile-up under the second condition may also be provided separately, and a counted number therein may be used. The provided X-ray detector cannot be said to be a photon counting type detector.

All parameters or characteristic data may not be experimentally determined, but some of the parameters or the characteristic data may be determined in computation through simulation.

Sixth Embodiment

In the above-described embodiments, a description has been made of a case where raw data is corrected by using a counting error amount due to pile-up, but the influence of pile-up may be specified as a change in the sensitivity, and, in this case, a sensitivity distribution may be corrected by using a counting error amount.

In other words, in the present embodiment, a correction unit includes a counted number correction portion which corrects a counted number in the X-ray detection element by using an X-ray sensitivity distribution and/or an X-ray distribution. The counted number correction portion corrects the X-ray sensitivity distribution and/or the X-ray distribution by using a counting error amount determined by a counting error amount determination part, and corrects the counted number in the X-ray detection element by using the corrected X-ray sensitivity distribution and/or X-ray distribution.

Figure 17:
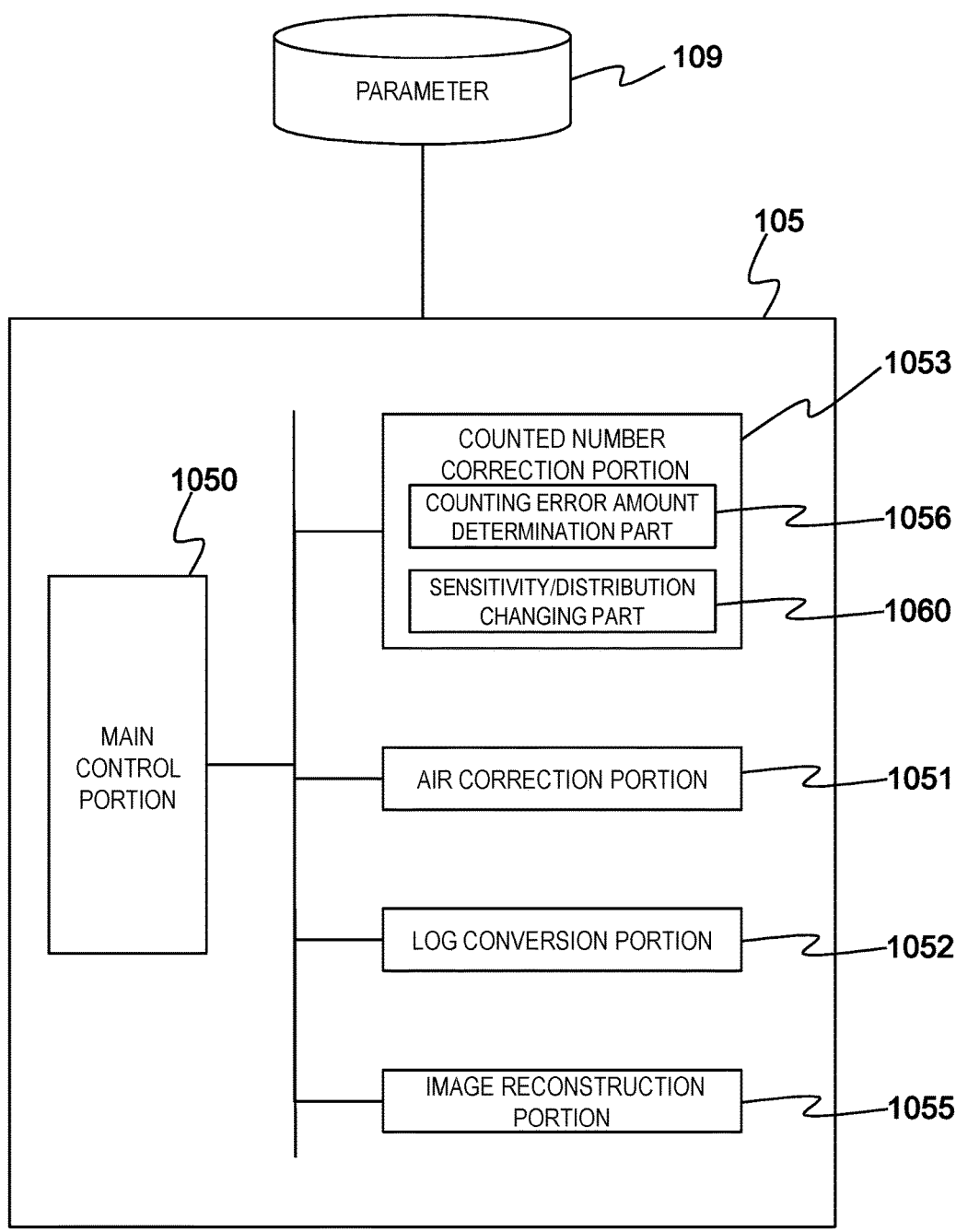
FIG. 17 is a functional block diagram mainly illustrating a configuration of a calculation unit in a sixth embodiment.

FIG. 17 illustrates a functional block diagram of the calculation unit 105 of the X-ray CT apparatus according to the present embodiment. In FIG. 17, the same constituent elements as the constituent elements illustrated in FIG. 6 or 13 which is referred to in description of the first or third embodiment are given the same reference numerals, repeated description thereof will be omitted, and description will be made focusing on differences.

As illustrated in FIG. 17, the calculation unit 105 includes a counted number correction portion 1053, and the counted number correction portion 1053 includes a counting error amount determination part 1056 and a sensitivity/X-ray distribution data changing part 1060. The parameter calculation part 1058 indicated by a dotted line is not necessary in an aspect in which parameters are calculated through simulation, but is necessary in an aspect in which some or all of the parameters are calculated on the basis of actually measured raw data.

The sensitivity/X-ray distribution data changing part 1060 changes sensitivity/X-ray distribution data used for air correction by using a counting error amount determined by the counting error amount determination part 1056.

Hereinafter, with reference to FIG. 18, a description will be made of a process performed by the calculation unit 105 of the present embodiment.

First, a counting error amount is determined by using actually measured raw data 143 (S1011). As a technique of determining a counting error amount, anyone of various techniques (formulae) described in the above-described first to fifth embodiments may be employed, and parameters stored in the storage unit 109 in advance are used as the parameters 141 depending on an employed formula.

Next, the sensitivity/X-ray distribution data changing part 1060 changes sensitivity/X-ray distribution data 142 saved in the storage unit 109 in advance by using the determined counting error amount, and creates sensitivity/X-ray distribution data 139 including the influence of pile-up (S1012). Specifically, the sensitivity/X-ray distribution data 139 is created according to Equation (16).

[Equation 16]

$$Map_{correct}(i) = Map_{original}(i) \cdot B_{normalized}(i) \qquad (16)$$

In Equation (16), $Map_{correct}(i)$ indicates the sensitivity/X-ray distribution data 139 after being changed, $Map_{original}(i)$ indicates the sensitivity/X-ray distribution data 142 before being changed, and $B_{normalized}(i)$ indicates a ratio in which an output from the X-ray detection element is reduced due to a counting error. Here, first, for example, $B_{normalized}(i)$ may be calculated by subtracting a value from 1, the value being obtained by normalizing, with an ideal counted number having no counting error, a counting error amount which is calculated on the basis of a pile-up occurrence probability according to the above-described method. Computation using Equation (16) is performed for each energy range. Here, the sensitivity/X-ray distribution data 142 before being changed may be a sensitivity/X-ray distribution image which is created from an image captured at a dose not including the influence of pile-up, and may be a function representing input and output characteristics in a case of not including the influence of pile-up.

In the process (S1012), a change in an output due to a counting error in the raw data 143 is reflected in correction data used for air correction 132. For example, in a case where an output from the X-ray detection element 400 in the raw data 143 is reduced by 10% due to a counting error, the sensitivity/X-ray distribution data 142 is reduced by 10% so as to become 0.9 times, and thus the sensitivity/X-ray distribution data 139 including the influence of pile-up is created. The sensitivity/X-ray distribution data 139 after being changed is saved in the storage unit 109 (S1013).

Subsequent processes (S1014) to (S1017) are the same as the processes (S702) to (S705) in FIG. 7.

According to the present embodiment, the air correction 132 is performed by using the sensitivity/X-ray distribution data 139 including the influence of pile-up, and thus sensitivity or an X-ray distribution is corrected, and the influence of a counting error due to pile-up is also corrected.

Seventh Embodiment

In the above-described respective embodiments, a case where a sampling period of time for reading a signal from an X-ray detection element changes has not been described, but the present invention is also applicable to a case where a sampling period of time changes.

Here, the sampling period of time is time required for sampling performed once, and indicates a time width (interval) of, for example, each of the sampling periods of time 123, 124 and 125 in FIG. 4.

Generally, as long as pile-up does not occur, if a sampling period of time is long, energy of incident X-rays can be accurately measured, but, if a sampling period of time is short, a pile-up occurrence probability is reduced. Therefore, there may be a case where a sampling period of time is changed depending on energy of X-rays, and thus a pile-up occurrence probability changes due to changing of the sampling period of time. The present embodiment handles such changing of a sampling period of time.

In other words, the X-ray CT apparatus of the present embodiment includes a sampling adjustment unit which adjusts a sampling period of time (a period of time in which an output signal from an X-ray detection element is sampled so that it is determined whether or not an X-ray is detected, and, in a case where an X-ray is detected, an energy range is classified) in a signal collecting unit (reading circuit), and a counting error amount determination part determines a counting error amount for each of a plurality of sampling periods of time which can be adjusted by the sampling adjustment unit. Here, as a method of changing a sampling period of time, for example, there may be a method of changing a clock cycle, or a method of changing the number of clocks in a sampling period of time.

When a sampling period of time is changed, it is preferable to change a circuit constant of the reading circuit or a measurement parameter suitable for the sampling period of time. Regarding a parameter changed when a sampling period of time is reduced, preferably, a shaping time is reduced in a case where a shaping amplifier is used in the reading circuit, and an integral time is reduced in a case where an integrator is used. For this, capacity, resistance, inductance, or the like of a circuit filter may be changed. In a case where a comparator is used to classify energy, a determination time or a comparison number may be reduced to be optimized in accordance with a sampling period of time, and, in a case where an analog-digital converter is used, a conversion time or the number of bits may be reduced to be optimized in accordance with a sampling period of time. Various circuit constants of the reading circuit or various measurement parameters may be changed.

The X-ray CT apparatus of the present embodiment further includes an input unit which allows a user to select a condition related to adjustment of a sampling period of time, and the sampling adjustment unit adjusts a sampling period of time according to a condition which is input via the input unit.

FIG. 19 illustrates a schematic configuration of the X-ray CT apparatus of the present embodiment. In FIG. 19, the same constituent elements as the constituent elements illustrated in FIG. 1 which is referred to in description of the first embodiment are given the same reference numerals, repeated description thereof will be omitted, and description will be made focusing on differences.

As illustrated in FIG. 19, in the X-ray CT apparatus of the present embodiment, the signal collecting unit 108 has a configuration of switching between a plurality of sampling periods of time, and includes a sampling adjustment unit 117 which switches between a plurality of sampling periods of time. The sampling adjustment unit 117 may be a part of the control unit 107, and may be a circuit or a mechanism independent from the control unit 107.

Configurations of the calculation unit 105 and the storage unit 109 may be a configuration in which the parameters 141 used for the counting error amount determination part 1056 to determine a counting error amount are computed in advance through simulation are stored in the storage unit 109 as illustrated in FIG. 1, or a configuration in which the counted number correction portion 1053 includes the parameter calculation part 1058 which calculates parameters according to actually measured values as illustrated in FIG. 13. As illustrated in FIG. 17, the sensitivity distribution changing part 1060 may be provided instead of the counting error amount correction part 1057.

Changing of a sampling period of time in the sampling adjustment unit 117 may be performed, for example, by directly inputting a value to a user interface formed of the input unit 110 and the display unit 106, and may be in conjunction with changing of a scanning condition to be set. Scanning conditions related to a sampling period of time may include, for example, a condition in which a dose ratio (a dose of an incident X-ray per unit time) changes, such as a tube current, a tube voltage, a scanning part, and an object, a condition in which energy determination accuracy may possibly be changed, such as an energy range, the number of energy ranges, and energy determination accuracy, and a view time, a scanning time, and the number of captured images (used for reconstruction). Here, as the condition in which energy determination accuracy may possibly be changed, such as an energy range, the number of energy ranges, and energy determination accuracy, there may be whether or not contrast scanning is performed, and the type of contrast agent.

FIG. 20 illustrates an example of a user interface 170 for setting the above-described scanning conditions.

The user interface 170 shows conditions related to only changing of a sampling period of time, but, needless to say, conditions other than the conditions are provided on the same screen or a separate screen in the user interface. The scanning conditions or numerical values illustrated in FIG. 20 are only examples and are not intended to limit the present invention.

In the user interface 170, a sampling period of time can be directly changed by using changing means 175. It is possible to change a tube current with changing means 171, a tube voltage with changing means 172, a scanning part with changing means 173, an object with changing means 174, whether or not contrast scanning is performed with changing means 181, and the type of contrast agent with changing means 182. Further, it is possible to change the number of energy ranges with changing means 176, and each energy range with changing means 177. In this case, rows of energy ranges of the changing means 177 are increased in conjunction with the number of energy ranges. In other words, when the number of energy ranges N (where N is an integer of 2 or more) is input to the changing means 176, the changing means 177 of N rows (first to N-th energy ranges) up to the N-th energy range are displayed.

In such changing means, an item determined through selection may be directly input, and there is a condition which is uniquely determined if one or a plurality of items are determined. For example, if a view time and a scanning time are input, the number of captured images is uniquely determined.

As input means (input unit 106) for the user interface, various means such as a mouse, a keyboard, a touch panel, and a voice input may be used. Changing of a sampling period of time may be performed according to a measured number of incident photons instead of using the user interface. Changing of a sampling period of time may be performed in a part or the whole of the X-ray detectors 104.

On the other hand, the parameter calculation part 1058 calculates parameters (for example, $\alpha_{hn}$ and $\beta_{hn}$ in Equation (3)) for determining a counting error amount for each sampling period of time which can be adjusted by the sampling adjustment unit 117, and saves the parameters in the storage unit 109. Alternatively, parameters are calculated for each sampling period of time through simulation by using a computer which is separate from the X-ray CT apparatus, and are saved in the storage unit 109.

During scanning, the counting error amount determination part 1056 reads corresponding parameters from the storage unit 109 according to a sampling period of time changed by the sampling adjustment unit 117, determines a counting error amount, and performs correction of the counting error amount (a process performed by the counting error amount correction part 1057) or correction of a sensitivity distribution or the like (a process performed by the sensitivity/distribution correction part 1060).

According to the present embodiment, since a counting error amount can be determined by using appropriate parameters whenever a sampling period of time is changed, it is possible to accurately reflect a pile-up occurrence probability and thus to perform highly accurate correction.

Application Examples

In the above-described respective embodiments and modification examples thereof, a medical X-ray CT apparatus has been described as an example, but the present invention is not limited thereto, and may be applied to all apparatuses mounted with a photon counting type radiation detector which classifies radiation incident to a detection element depending on an energy range and counts the number of photons. Examples of apparatuses to which the present invention is applied may include an X-ray CT apparatus for non-destructive inspection, an X-ray cone-beam CT apparatus, a dual energy CT apparatus, an X-ray imaging diagnostic apparatus, an X-ray imaging scanning apparatus, a fluoroscopic apparatus, a mammographic apparatus, a digital subtraction apparatus, a nuclear medicine examination apparatus, and a radiation therapy apparatus. The present invention is not limited to an X-ray detector, and may also be applied to a photodetector which detects photons with various wavelengths. In this case, light may be visible light, infrared light, ultraviolet light, or gamma rays, and may have any wavelength.

The present invention is not limited to the above-described embodiments, and may be variously modified and implemented in the implementation stage within the scope without departing the spirit thereof. The above-described embodiments include various steps, and thus various embodiments may occur through an appropriate combination of a plurality of disclosed constituent elements. For example, some constituent elements may be deleted from all the constituent elements described in the embodiments.

INDUSTRIAL APPLICABILITY

According to the present invention, it is possible to provide a scanning apparatus including a photon counting type detector, and improving the quantitativeness of obtained image quality or amounts.

REFERENCE SIGNS LIST

100 X-RAY SOURCE, 101 GANTRY ROTATION UNIT, 102 X-RAY COLLIMATOR, 103 BED TOP PLATE, 104 X-RAY DETECTOR, 105 CALCULATION UNIT, 106 DISPLAY UNIT, 107 CONTROL UNIT, 108 SIGNAL COLLECTING UNIT, 109 STORAGE UNIT, 110 INPUT UNIT, 113 X-RAY FILTER, 114 DOSE CHANGING UNIT, 115 RAY QUALITY CHANGING UNIT, 123 TO 125 SAMPLING PERIOD OF TIME, 170 USER INTERFACE, 171 TO 182 CHANGING MEANS, 400 X-RAY DETECTION ELEMENT, 405 READING CIRCUIT, 1050 MAIN CONTROL PORTION, 1051 AIR CORRECTION PORTION, 1052 LOG CONVERSION PORTION, 1053 COUNTED NUMBER CORRECTION PORTION, 1056 COUNTING ERROR AMOUNT DETERMINATION PART, 1057 COUNTING ERROR AMOUNT CORRECTION PART, 1058 PARAMETER CALCULATION PART, 1060 SENSITIVITY/DISTRIBUTION CORRECTION PART, 117 SAMPLING ADJUSTMENT UNIT

The invention claimed is:

1. An X-ray scanning apparatus comprising:
   an X-ray detector in which a plurality of photon counting type X-ray detection elements are disposed, each of the X-ray detection elements detecting an incident X-ray photon, classifying energy of the X-ray photon into two or more energy ranges, and counting the X-ray photon;
   a signal collecting unit that collects a counted number in the X-ray detection element;
   a correction unit that corrects the counted number in the X-ray detection element and creates projection data; and
   an image reconstruction unit that performs reconstruction calculation on the projection data so as to create a reconstructed image,
   wherein the correction unit includes a counting error amount determination part that determines a counting error amount in a counted number due to pile-up on the basis of a pile-up occurrence probability in two or more X-ray photons.

2. The X-ray scanning apparatus according to claim 1, wherein the pile-up occurrence probability is determined by using a product of counted numbers measured in energy ranges in which two or more X-ray photons related to a single pile-up are respectively included.

3. The X-ray scanning apparatus according to claim 1, wherein the counting error amount determination part determines the counting error amount on the basis of a product of a change amount of the counted number due to a single pile-up and the pile-up occurrence probability.

4. The X-ray scanning apparatus according to claim 3, wherein the counting error amount determination part determines a decrease amount (counting omission) due to a single pile-up in a counting error amount in a single energy range by using a counted number measured in the single energy range and counted numbers measured in energy ranges other than the single energy range.

5. The X-ray scanning apparatus according to claim 3, wherein the counting error amount determination part determines an increase amount (counting redundancy amount) due to a single pile-up in a counting error amount in a single energy range by using a counted number measured in an energy range lower than the single energy range.

6. The X-ray scanning apparatus according to claim 3, further comprising:
   a storage unit that stores a parameter including information regarding a change amount due to the single pile-up,
   wherein the counting error amount determination part determines the counting error amount by using the parameter stored in the storage unit and counted numbers measured in energy ranges in which two or more piled-up X-ray photons are respectively included.

7. The X-ray scanning apparatus according to claim 6, wherein the X-ray detector is formed of the M (where M is an integer of 2 or more) X-ray detection elements,
   wherein each of the X-ray detection elements classifies energy into first to N-th (where N is an integer of 2 or more) energy ranges in an increasing order of the energy,
   wherein the storage unit stores parameters $\alpha_{jk}(i)$ and $\beta_{gh}(i)$ (where i is an integer of 1 to M, and j, k, g, and h are integers of 1 or more, indicating the energy ranges), and wherein, when a measured counted number in an n-th (where n is an integer of 1 to N) energy range is indicated by $R_n(i)$, the counting error amount determination part determines the counting error amount $B_n(i)$ by using the following formula:

if $n = N$ $$B_n(i) = -\alpha_{nN} R_N(i) R_n(i) + \sum_{g=1}^{n-1} \sum_{h=g}^{n-1} \beta_{gh} R_g(i) R_h(i)$$

if $n = 2$ to $(N - 1)$ (where $N$ is only 3 or more)

$$B_n(i) = -\sum_{h=1}^{N} \alpha_{hn} R_h(i) R_n(i) + \sum_{g=1}^{n-1} \sum_{h=g}^{n-1} \beta_{gh} R_g(i) R_h(i)$$

if $n = 1$ $$B_n(i) = -\sum_{h=1}^{N} \alpha_{hn} R_h(i) R_n(i).$$

8. The X-ray scanning apparatus according to claim 1, wherein the pile-up occurrence probability is determined on the basis of a sum of counted numbers of X-ray photons in all energy ranges.

9. The X-ray scanning apparatus according to claim 8, wherein the counting error amount determination part determines the counting error amount by using a product of the pile-up occurrence probability determined on the basis of the sum of counted numbers of X-ray photons in all energy ranges, and a parameter which is calculated in advance.

10. The X-ray scanning apparatus according to claim 9, further comprising:
a parameter calculation part that calculates the parameter, wherein the parameter calculation part calculates the parameter by using counted numbers in respective energy ranges which are obtained through measurement or simulation under two or more different conditions related to the occurrence of pile-up.

11. The X-ray scanning apparatus according to claim 2, wherein the counting error amount determination part determines the counting error amount by using a characteristic function including a product term of the counted numbers.

12. The X-ray scanning apparatus according to claim 11, wherein the characteristic function is calculated by using counted numbers in respective energy ranges which are obtained through measurement or simulation under two or more different conditions related to the occurrence of pile-up.

13. The X-ray scanning apparatus according to claim 12, wherein the two or more conditions related to the occurrence of pile-up include a condition regarding a dose of X-ray incident to the X-ray detector.

14. The X-ray scanning apparatus according to claim 13, wherein one of the two or more conditions related to the occurrence of pile-up is a condition in which a dose of X-ray incident to the X-ray detector does not cause pile-up.

15. The X-ray scanning apparatus according to claim 1, further comprising:
a sampling adjustment unit that adjusts a sampling period of time in the X-ray detection element,
wherein the counting error amount determination part determines a counting error amount for each of a plurality of sampling periods of time which can be adjusted by the sampling adjustment unit.

16. The X-ray scanning apparatus according to claim 15, further comprising:
an input unit that allows a user to select a condition related to the sampling period of time,
wherein the sampling adjustment unit adjusts the sampling period of time according to a condition which is input via the input unit.

17. The X-ray scanning apparatus according to claim 1, wherein the correction unit includes a counting error amount correction part that corrects a counted number in the X-ray detection element by using the counting error amount determined by the counting error amount determination part.

18. The X-ray scanning apparatus according to claim 1, wherein the correction unit includes
a sensitivity distribution changing part that changes a preset X-ray sensitivity distribution and/or X-ray distribution by using the counting error amount determined by the counting error amount determination part; and
an air correction part that corrects a counted number in the X-ray detection element by using the changed X-ray sensitivity distribution and/or X-ray distribution.

19. The X-ray scanning apparatus according to claim 6, further comprising:
a parameter calculation part that calculates the parameter, wherein the parameter calculation part calculates the parameter by using counted numbers in respective energy ranges which are obtained through measurement or simulation under two or more different conditions related to the occurrence of pile-up.

* * * * *